(12) United States Patent
Abel et al.

(10) Patent No.: US 6,329,487 B1
(45) Date of Patent: Dec. 11, 2001

(54) SILAZANE AND/OR POLYSILAZANE COMPOUNDS AND METHODS OF MAKING

(75) Inventors: Albert E. Abel, Powell, OH (US); Tracy A. Kruger, Cambridge, MA (US); Robert W. Mouk, Westerville; Gary J. Knasiak, Columbus, both of OH (US)

(73) Assignee: Kion Corporation, Columbus, OH (US)

( * ) Notice: Subject to any disclaimer, the term of this patent is extended or adjusted under 35 U.S.C. 154(b) by 0 days.

(21) Appl. No.: 09/439,871

(22) Filed: Nov. 12, 1999

(51) Int. Cl.$^7$ .................................................. C08E 77/08
(52) U.S. Cl. .............................. 528/21; 528/28; 528/31; 528/38; 556/412
(58) Field of Search ...................... 528/28, 31, 38, 528/21; 556/412

(56) References Cited

U.S. PATENT DOCUMENTS

| | | | |
|---|---|---|---|
| 4,255,549 | 3/1981 | Christophiemk | 528/28 |
| 4,395,460 | 7/1983 | Gaul | 428/408 |
| 4,482,669 | 11/1984 | Seyferth et al. | 524/442 |
| 4,720,532 | 1/1988 | Seyferth et al. | 528/28 |
| 4,788,309 | 11/1988 | Laine et al. | 556/412 |
| 4,954,596 | 9/1990 | Takeda et al. | 528/14 |
| 4,961,913 * | 10/1990 | Sullivan . | |
| 5,032,649 | 7/1991 | Schwark | 525/474 |
| 5,110,364 | 5/1992 | Mazur et al. | 134/2 |
| 5,250,648 * | 10/1993 | Huggins . | |
| 5,414,200 | 5/1995 | Mouk et al. | 588/205 |
| 5,708,114 * | 1/1998 | Barnard et al. . | |
| 5,998,691 | 12/1999 | Abel et al. | 588/200 |
| 6,049,021 | 4/2000 | Getman et al. | 588/1 |

FOREIGN PATENT DOCUMENTS

| | | |
|---|---|---|
| 737229 | 9/1955 | (GB) . |
| 968110 | 8/1964 | (GB) . |

OTHER PUBLICATIONS

Brewer, S., Haber, C., Journal of American Chemical Soc., 70, 3888–91 (1948).

Sauer, R, Hasek, R., Journal of American Chemical Soc., 68, 241–44 (1946).

Haiduc, I., Chemistry of Inorganic Ring Systems, 365–423, (1970).

Allcock, et al.; "Contemporary Polymer Chemistry, 2nd ed.", 1990, Prentice–Hall Inc. Englewood Cliffs, NJ 07632, p. 380.*

* cited by examiner

*Primary Examiner*—Robert Dawson
*Assistant Examiner*—Marc S. Zimmer
(74) *Attorney, Agent, or Firm*—Howard M. Ellis; Marianne Fuierer

(57) ABSTRACT

This invention is directed to novel ammonolysis products including novel silazanes and polysilazanes characterized by repeating units of silicon-nitrogen in a polymeric compound having a reduced amount of Si—H bonds relative to the amount of Si—H bonds in the starting compound. Preparation of these novel ammonolysis products comprises introducing a starting compound containing at least one Si—H bond, such as a halosilane into a stoichiometric excess of anhydrous liquid ammonia wherein an ammonium halide is generated acting as an acid catalyst to provide an ionic and/or acidic environment for preparing the novel ammonolysis compounds. The prepared novel ammonolysis products are retained in a separate liquid-phase layer and distinct from the anhydrous liquid ammonia containing the ionized ammonium halide. Also provided are methods to purify ammonolysis products and to modify ammonolysis products by controllably increasing viscosity from a liquid to a solid and viscosities there between.

63 Claims, 11 Drawing Sheets

SILAZANE AND/OR POLYSILAZANE COMPOUNDS AND METHODS OF MAKING

TECHNICAL FIELD

This invention relates generally to the preparation of ammonolysis products and more particularly to the synthesis of novel silazane and/or polysilazane compounds, including monomers, oligomers and polymers containing the Si—N structure in the molecule.

BACKGROUND OF THE INVENTION

Silazanes, which have a Si—N—Si bond configuration, are increasingly important because they can be pyrolyzed to yield ceramic materials, such as silicon carbide and silicon nitride.

Silazanes are usually synthesized by an ammonolysis process wherein ammonia or a primary amine is reacted with a halide substituted silane. The ammonolysis of organohalosilanes is a complex process consisting of several concurrent reactions as shown below. These formulas carry no structural implication, they merely are average formulations to illustrate the reactions such as:

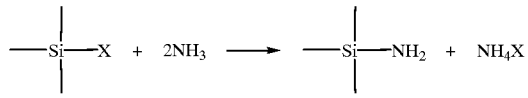

and Homo- and heterofunctional condensation.

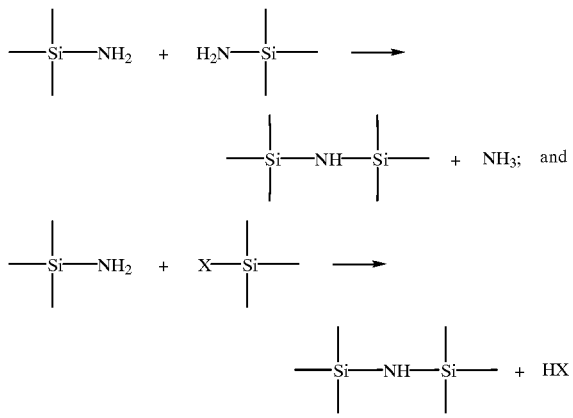

The preparation of silazanes by ammonolysis has been described in several U.S. patents. For instance, U.S. Pat. No. 4,395,460, issued to Gaul, describes a process for the preparation of polysilazanes in which gaseous ammonia is introduced to a solution of chlorodisilanes that have been dissolved in an inert solvent. However, during the reaction $NH_4Cl$ is precipitated concurrently with the formation of the ammonolysis products. The precipitated $NH_4Cl$ greatly increases the viscosity of the reaction mixture and interferes with the progress of the reaction. To overcome this problem, additional inert solvent must be added to the reaction mixture to facilitate agitation of the mixture. Furthermore, to recover a purified ammonolysis product several constituents of the reaction product mixture have to be removed. The precipitated $NH_4Cl$ formed during the reaction and intermixed with the ammonolysis products has to be removed by filtration and the filter cake washed with additional solvent for complete product recovery. Subsequently the inert solvent which is used for dissolving the chlorodisilanes, for reducing the viscosity of the reaction mixture, and for washing the filtered crystals must be removed from the preferred products.

U.S. Pat. No. 4,954,596, issued to Takeda et al, describes preparation of organosilazanes by introducing gaseous ammonia into a reaction mixture comprising organochlorosilanes dissolved in an organic solvent. However, the added organic solvent must be removed by distillation to isolate the silazane products. Likewise in U.S. Pat. No. 2,564,674, organochlorosilanes are dissolved in ether before the ammonolysis process and additional ether is added during the process to dissolve the silicon compounds and prevent their gelation. Again, purification of the final product requires several steps.

U.S. Pat. No. 4,255,549, issued to Christophliemk et al., describes reacting organohalosilanes, dissolved in an inert solvent, with liquid ammonia to form ammonolysis products. To maintain the reaction course and to prevent overheating due to a high heat of reaction and/or heat of crystallization of precipitating ammonium halide salt, an inert solvent is added to the reaction vessel. As a result of this addition, the solvent has to be evaporated under controlled conditions to produce the polymer films.

As apparent from the foregoing description, preparing silazane products by known ammonolysis methods leads to unwanted co-products, such as $NH_4Cl$ precipitates, that prompts the need for increased additions of inert solvent to the reaction mixture. The addition of the solvent is required to decrease the viscosity and improve agitation of the reaction slurry. Furthermore, an inert solvent is needed to reduce the heat of reaction and/or heat of crystallization due to precipitating ammonium halide salts. However, the $NH_4Cl$ precipitates must be filtered from the reaction slurry and the inert solvent removed from the final ammonolysis product.

Another problem encountered during the production of silazanes is the formation of a high proportion of low molecular weight species. These low molecular weight silazanes can evaporate during pyrolysis resulting in a reduced weight yield of the ceramic product relative to the starting silazane material. British patent, 737,229, issued to Midland Silicones Limited, describes a method for producing silazanes wherein organohalosilanes, completely substituted with organic groups and/or halogen atoms and dissolved in an inert solvent, are added simultaneously to ammonia under pressure. However, the majority of prepared organocyclosilazanes are limited by the starting compounds to only 3–4 Si—N linkage units and a low yield of polysilazanes. As such, the prepared silazanes are volatile and difficult to pyrolize to ceramic material.

Accordingly, there is a need for novel silazanes and/or polysilazanes having an increased number of Si—N units and for improved methods for preparing silazanes, and/or polysilazanes that provide a means to easily separate desired products from any unwanted co-products generated in the reaction, that do not require large quantities of inert solvent to be introduced into the reaction mixture, that moderate the reaction exotherm for quick and efficient ammonolysis and provide polysilazanes having an increased number of Si—N linkages.

SUMMARY OF THE INVENTION

For purposes of this invention, the terms and expressions appearing in the specification and claims, are intended to have the following meanings:

"Silazane" as used herein means monomers, oligomers, cyclic and linear polymers having one to four Si—N repeating units in the compound.

"Polysilazane" as used herein means oligomers, cyclic, polycyclic, linear polymers or resinous polymers having at least five Si—N repeating units in the compound.

"Ammonolysis products" as used herein is at least one member selected from the group including silazanes, polysilazanes, aminosilanes, organosilazanes, organopolysilazanes and mixtures thereof.

"Si—H starting compounds" as used herein is at least one member selected from the group including halosilanes, organohalosilanes, silazanes and/or polysilazanes, all of which have at least one Si—H bond.

"Anhydrous liquid ammonia" as used herein means anhydrous ammonia containing less water than an amount that will cause unwanted hydrolysis of the product.

It is an object of the present invention to provide novel compounds containing at least one Si—N unit.

It is another object of the present invention to provide improved methods of preparing both known and novel compounds containing at least one Si—N unit from starting compounds containing at least one Si—H bond.

Yet another object of the present invention is to provide novel liquid and solid compounds containing the Si—N unit having modifiable viscosity.

A further object of the present invention is to provide methods to catalytically polymerize novel and/or known silazanes and/or further polymerize polysilazanes.

A still further object is to provide a method for catalytically synthesizing known and/or novel silazanes and/or polysilazanes wherein a small amount of an acid catalyst is added to initiate the synthesis and thereafter the effective catalyst is generated in the ammonolysis reaction.

Another object of the present invention is to provide an improved method for preparing known and/or novel silazanes and/or polysilazanes wherein the prepared ammonolysis products are easily separated from the reaction mixture and do not require extensive purification for removal of unwanted by-products.

Yet another object of the present invention is to provide a method for preparing known and/or novel silazanes and/or polysilazanes without requiring the addition of inert solvents to dissolve the reactants, reduce increasing viscosity of the reaction mixture during ammonolysis or to moderate the heat of reaction and/or heat of crystallization of formed ammonium salts.

Still another object of the present invention is to provide methods for preparing known and/or novel silazanes and/or polysilazanes having viscosities ranging from liquid to solid. The silazanes and/or polysilazanes having at least one structural configurations including, but not limited to linear polymers, cyclic structures having at least four members and mixtures thereof.

A still further object of the present invention is to provide methods of purification to removed ammonium halide salts from prepared novel or known silazanes and/or polysilazanes.

The novel silazanes or polysilazanes prepared by the present invention are characterized by repeating units of silicon-nitrogen comprising a reduced amount of Si—H bonds relative to the quantity of Si—H bonds that are incorporated into the silazane or polysilazane from Si—H bond containing starting compounds. The novel silazanes and/or polysilazanes are essentially free of metal impurities.

The novel silazanes and/or polysilazanes compounds of the present invention may be prepared by ammonolysis, the method comprising the following steps:

a) introducing at least one halosilane having at least one Si—H bond into liquid anhydrous ammonia, the amount of liquid anhydrous ammonia being at least twice the stoichiometric amount of silicon-halide bonds on the halosilane, the halosilane reacting with the anhydrous liquid ammonia to form a precursor ammonolysis product and an ammonium halide salt or acid thereof, the ammonium halide salt or acid thereof being solubilized and ionized in the anhydrous liquid ammonia thereby providing an acidic environment; and b) maintaining the precursor ammonolysis product in the acidic environment for a sufficient time to reduce the number of Si—H bonds relative to the quantity of Si—H bonds that are incorporated into the novel silazane and/or polysilazane from the halosilane of step (a).

The anhydrous liquid ammonia is maintained at a sufficient temperature and/or pressure to remain in a liquefied state, and preferably, between about −33° C. to about 130° C. As a result, the anhydrous ammonia in a liquefied state acts as a reactive solvent which not only participates as a nucleophile in the nucleophilic attack on the halosilane, but also solubilizes and retains a substantial amount of ammonium halide salt produced during ammonolysis.

While not wishing to be bound by any particular theory of operation, it is believed that by retaining the solubilized and ionized ammonium halide in the liquid ammonia solution, the ionized salt acts as an effective catalyst in the different and novel polymerization process of the present invention.

It has been observed that initially the reaction proceeds in a homogenous phase wherein the generated ammonium halide salt is solubilized and ionized in the anhydrous liquid ammonia thereby reducing precipitation of ammonium halide salt. As such, solubilization of ammonium chloride avoids contamination of the ammonolysis products with precipitating salts and eliminates the need for introducing an inert solvent to reduce the viscosity of the reaction mixture. Additionally, solubilization of the ammonium halide salt ameliorates the heat of crystallization of the salt which is a problem found in the prior art.

Moreover, we have found that there is no requirement for dissolving the starting compounds in an inert solvent before injection, such as in the methods disclosed in the prior art and the Si—H bond containing starting compounds can be injected directly into the anhydrous liquid ammonia.

It has been observed that during and upon completion of the ammonolysis process, which is time dependent on the preferred viscosity and degree of polymerization of the ammonolysis products, the reaction mixture forms a two-phase system wherein the prepared ammonolysis products collect in a distinct liquid-phase layer separate from the anhydrous liquid ammonia solution containing the solubilized ammonium halide salt.

The two-phase system provides for easy separation of the ammonolysis products from the liquid ammonia layer by draining or decanting the silazanes and/or polysilazanes. In the alternative the liquid ammonia containing the solubilized ammonium chloride salt may be drained or decanted from the system. During the process, the liquid ammonia may be removed continuously as long as it is replaced with additional anhydrous liquid ammonia. The continuous draining or decanting of ammonia during the process prevents saturation of the liquid ammonia with ionized ammonium halide salt and allows the reaction to proceed without precipitation of ammonium halide salts.

The starting compounds having at least one Si—H bond may include at least one halosilane, and more preferably the halosilane may be selected from the group consisting of $RSiX_3$, $R_2SiX_2$, $R_3SiX$, and mixtures thereof wherein R may be identical or different from each other and selected from the following group including a hydrogen atom, a substituted or unsubstituted alkyl group, a substituted or unsubstituted cycloalkyl group, a substituted or unsubstituted alkenyl group and a substituted or unsubstituted aryl group, with the proviso that at least one R is a hydrogen atom; and X is a halogen selected from the group of fluorine, iodine, chlorine and bromine. Additionally halogen substituted disilanes may be present.

It should be noted that the present invention may further comprise a mixture of halosilanes wherein a percentage of the halosilanes have a Si—H bond and the remaining percentage of halosilanes lack a Si—H bond.

In another embodiment of the present invention, known ammonolysis products may be prepared from any halogen substituted silane, along with known silazanes such as tetramethyldisilazane and known polysilazanes as taught in the prior art. The method of preparation comprises introducing at least one halogen substituted silane into anhydrous liquid ammonia, the amount of liquid anhydrous ammonia being at least twice the stoichiometric amount of silicon-halide bonds on the halogen substituted silane, the halogen substituted silane reacting with the anhydrous liquid ammonia to form an ammonolysis product and an ionic by-product solubilized in the anhydrous liquid ammonia.

The anhydrous liquid ammonia is maintained at a sufficient temperature and/or pressure to remain in a liquefied state.

An ionizable salt may be introduced into the anhydrous liquid ammonia before the halogen substituted silane is injected into the liquid ammonia solution to provide an ionic environment. The ionizable salt may be any compound that is solubilized and/or ionized in anhydrous liquid ammonia, including, but not limited to inorganic salts, such as a ammonium salt including ammonium halide and ammonium nitrate; and organic salts, such as ammonium acetate.

The prepared ammonolysis products can be easily separated from the anhydrous liquid ammonia solution in that they collect in a distinct liquid-layer away from the anhydrous liquid ammonia layer which contains the solubilized ionic by-product.

Any halogen substituted silane that undergoes ammonolysis may be used in this method. Preferably a halosilane is selected from the group consisting of $RSiX_3$, $R_2SiX_2$, $R_3SiX$, and mixtures thereof wherein R may be identical or different from each other and selected from the following group including a hydrogen atom, a substituted or unsubstituted alkyl group, a substituted or unsubstituted cycloalkyl group, a substituted or unsubstituted alkenyl group, a substituted or unsubstituted aryl group and mixtures thereof, and X is a halogen. Tetrafunctional silanes $SiX_4$ may additionally be present as well as halogen substituted disilanes.

Advantageously, the present process does not require the halogen substituted silane to be dissolved in an inert solvent before introducing into the anhydrous liquid ammonia which eliminates the necessity of evaporating any solvent from the final product.

The ammonolysis products synthesized using the methods of the present invention are essentially noncontaminated with ammonium halide salts. However, in some instances, there may be ammonium halide salt remaining in the end product. As such, it would be beneficial to easily separate the ammonium halide salt from the prepared product.

Accordingly, in yet another embodiment of the present invention, a method is provided to purify silazanes and polysilazanes by removing essentially all ammonium halide salts. The silazanes and/or polysilazanes may be prepared by the methods of the present invention or by methods of the prior art and further purified by the steps comprising:

a) mixing an ammonolysis product containing an ammonium halide salt with a sufficient amount of anhydrous liquid ammonia to solubilize the ammonium halide salt in the anhydrous liquid ammonia; and b) separating a purified ammonolysis product from the anhydrous liquid ammonia.

Separation of the purified ammonolysis product is easily accomplished because the ammonolysis product is retained in a separate liquid layer distinct from the anhydrous liquid ammonia containing the solubilized ammonium halide salt.

In the alternative, the purification method may comprise a) mixing an ammonolysis product containing an ammonium halide salt with a sufficient amount of anhydrous liquid ammonia to solubilize the ammonium halide salt in the anhydrous liquid ammonia; and b) adding an alkali metal or alkaline earth metal to the anhydrous liquid ammonia in a sufficient amount to react with the ammonium halide salt to produce an alkali metal or alkaline earth halide salt.

The alkali metal or alkaline earth halide salt is essentially neutral, and as such, will not effect the ammonolysis products. Separation of the purified ammonolysis product may be accomplished by separation methods well known to those skilled in the art.

A still further embodiment of the present invention provides a method to further polymerize ammonolysis products, whether produced by methods of the prior art or by the present invention, with the proviso that the ammonolysis product to be further polymerized has an "Si—H" site. Further polymerization is carried out catalytically using an acid catalyst which is effective in activating the Si—H bond, the method comprising the steps of:

a) providing a solution of anhydrous liquid ammonia having solubilized and/or ionized therein an acid catalyst which is effective in cleaving a Si—H bond, the solubilized and/or ionized acid catalyst providing an acidic environment in the anhydrous liquid ammonia solution;

b) introducing an ammonolysis product having at least one Si—H bond directly into a stoichiometric excess of liquid anhydrous ammonia; and c) maintaining the ammonolysis product in the acidic environment for a sufficient time to reduce the amount of Si—H bonds relative to the amount in the ammonolysis product in step (b) and to polymerize, and/or copolymerize and/or rearrange ammonolysis products.

The acid catalyst may be any nonmetallic acid or salt thereof that is solubilized and/or ionized in anhydrous liquid ammonia and that generates an acidic environment in anhydrous liquid ammonia, including, but not limited to inorganic salts, such as ammonium halide and ammonium nitrate; and organic salts, such as ammonium acetate, and a mixture thereof.

The mechanism for further polymerization of ammonolysis products is not yet completely understood. Unexpectedly, the further polymerization can be effected without active silicon-halogen (Si—Cl)ammonolysis sites on the starting compound having a Si—H bond. It is believed that heterolytic cleavage of the Si—H bond provides a route for further ammonolysis of a silazane and/or polysilazane. The ammonolysis process can continue until all active Si—H sites are cleaved and reacted and/or the preferred viscosity is achieved.

Yet another embodiment of the present invention provides for an alternative method to modify the viscosity of liquid and/or gel-like ammonolysis products from a few centipoise to a solid material. The ammonolysis products to be modified may be previously prepared by the methods of the present invention or by other methods well know in the art. The modifying process comprises:

a) introducing the liquid and/or gel-like ammonolysis product into a sufficient amount of anhydrous liquid ammonia to dissolve the ammonolysis product therein;

b) introducing a catalytically effective amount of an alkali or alkaline earth metal into the anhydrous liquid ammonia containing the ammonolysis product, the alkali or alkaline earth metal producing solvated electrons and cations therein; and c) maintaining the ammonolysis product in the anhydrous liquid ammonia for a sufficient time to increase the viscosity of the ammonolysis product.

When the desired viscosity of the ammonolysis product is reached the modification can be quenched by the addition of a sufficient amount of an acidic reagent, such as an ammonium salt. The modified ammonolysis products can be separated from the anhydrous liquid ammonia by any separation method known in the art.

Other features and advantages of the present invention will be apparent from the following description of the preferred embodiments thereof and from the claims.

DETAILED DESCRIPTION OF THE PREFERRED EMBODIMENT

Figure 1:
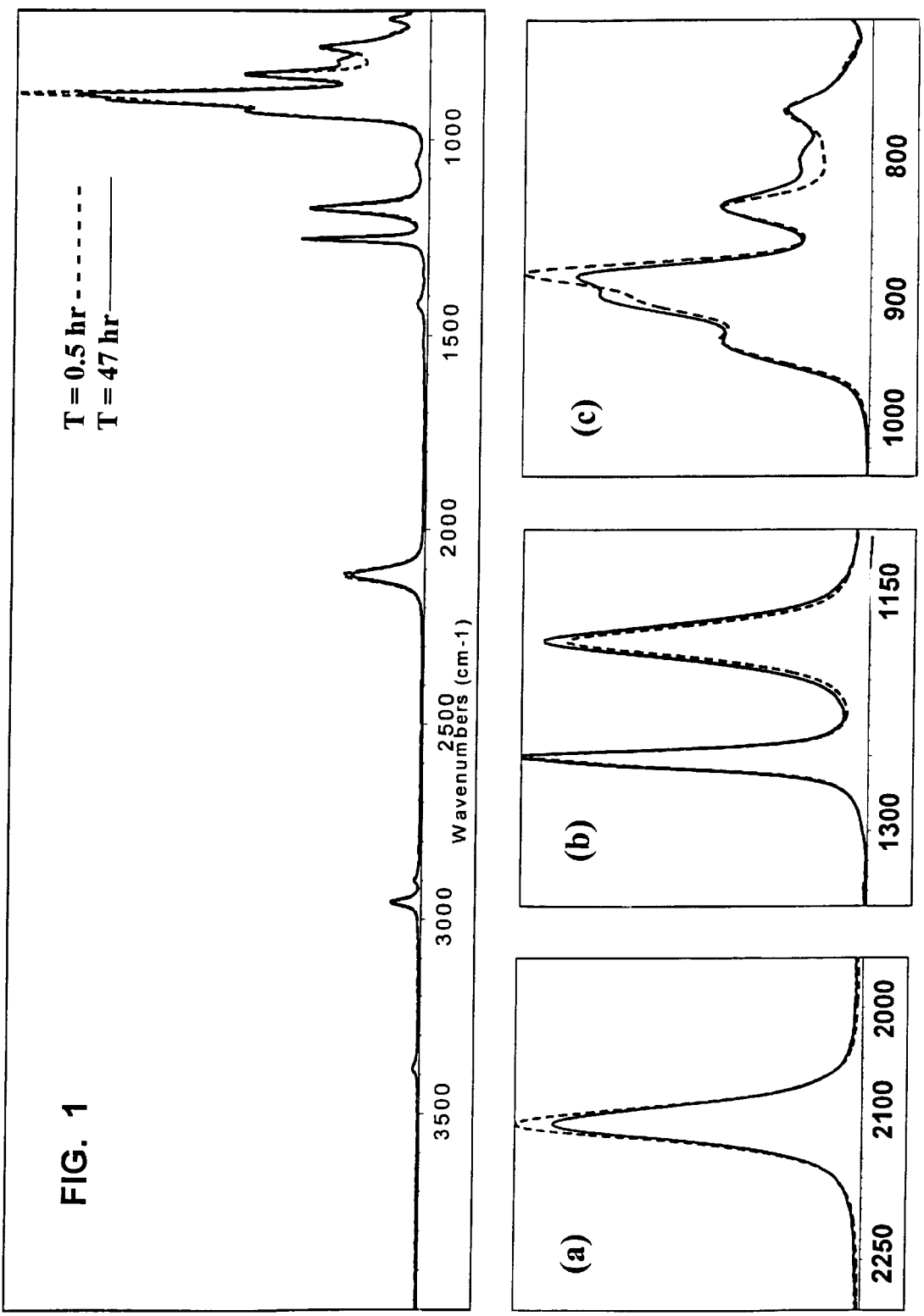
FIG. 1 graphically represents the Fourier Transform Infrared (FTIR) spectra of prepared and further polymerization of tetramethyldisilazane over a time period of 47 hours.

The novel silazanes and/or polysilazanes of the present invention are characterized by having a decreased number of silicon-hydrogen bonds relative to the amount of Si—H bonds contained in the starting compounds. For example, if ten halosilane molecules, each having a Si—H bond, are incorporated into and form a novel polysilazane having at least ten Si—N linkages then this novel polysilazane will have less than ten Si—H bonds. The reduction in Si—H bonds can range from about 10% to about 90% relative to the number of Si—H bonds contained in the starting compounds. The viscosity of the novel silazanes and/or polysilazane will be proportional to the reduction of Si—H bonds relative to the amount of Si—H bonds contained in the starting compounds. Additionally, there may be a proportional increase in Si—N linkages relative to the reduction in Si—H bonds. These novel silazanes and/or polysilazanes are believed to comprise several different structures including linear structures, and fused rings having at least four members. Representative examples of a six and eight membered fused rings are shown in structures (1) and (2) and a linear structure is shown in Scheme (III). All of these structures represent the novel silazanes and/or polysilazanes formed by the process of the present invention wherein R may be identical or different from each other, and selected from the group including a hydrogen atom, a substituted or unsubstituted alkyl group, a substituted or unsubstituted cycloalkyl group, a substituted or unsubstituted alkenyl group or a substituted or unsubstituted aryl group and n is 1 or greater.

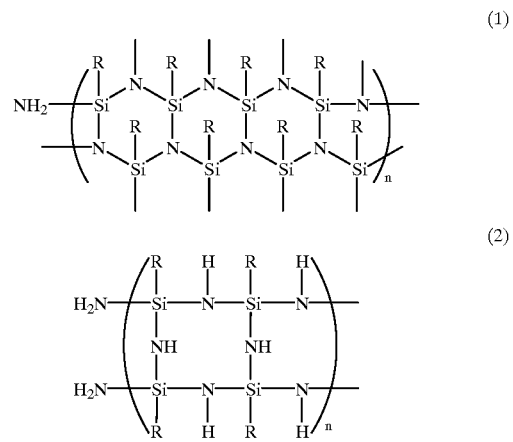

While not wishing to be bound by theory, it is believed that the initial reaction leading to the formation of these novel ammonolysis products may be represented generally by the following Scheme I covering a possible mechanistic route using a Si—H bond containing starting compound such as methyldichlorosilane:

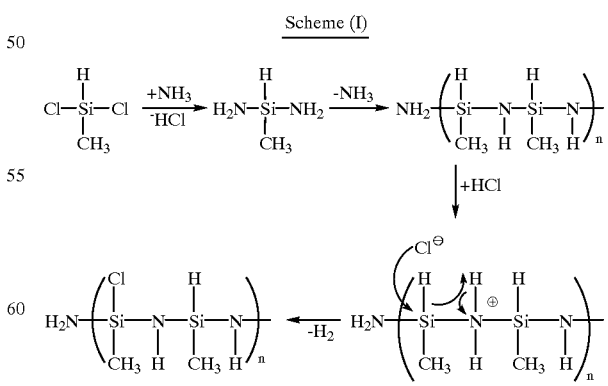

During the initial ammonolysis, the silicon-chlorine bonds undergo ammonolysis generating a diaminosilane which is further converted into a linear molecule containing several Si—N structural units. The linear structure is stabilized in the anhydrous liquid ammonia containing an ionized ammonium halide salt dissolved therein. This ionized and dissolved ammonium halide salt acts as an acid catalyst which catalyzes a loss of a Si—H bond to generate a new silicon-chlorine bond on the straight chain of the polymer. The newly generated chlorosilane bond may undergo further ammonolysis. This reaction will proceed until virtually all chlorosilicon bonds are ammonolyized as shown below in Scheme II.

Scheme (II)

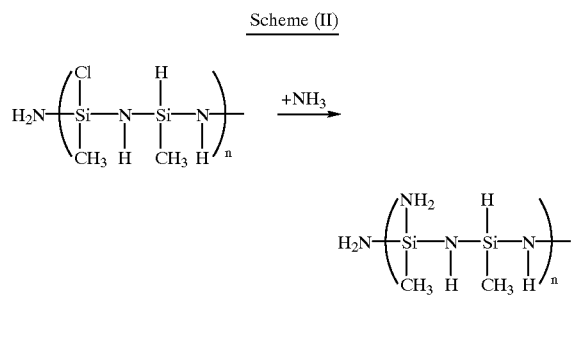

It is theorized that two linear structures can condense to form an eight membered planar ladder structure with a loss of ammonia such as shown below in Scheme III Scheme (III)

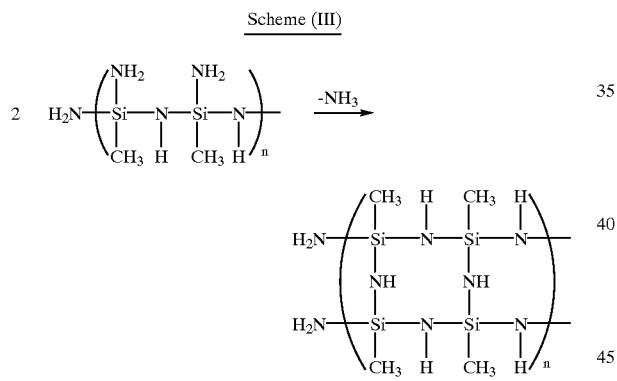

This ladder structure can undergo a further condensation whereby a nitrogen atom attacks a remote silicon atom displacing a N—H bond which then protonates to generate a six membered ring in which a newly generated $NH_2$ group appends to a silicon atom such as shown below in scheme (IV).

Scheme (IV)

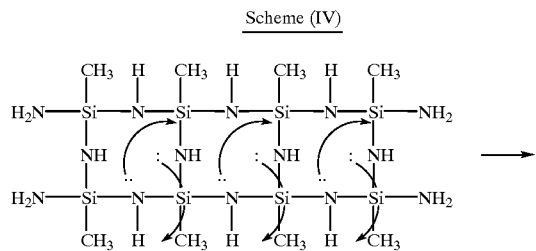

-continued

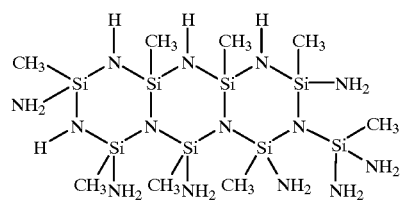

This cyclic structure can dimerize or add a linear group to generate an approximate planar structure with an appended eight member ring that can further condense to a fused six member ring such as shown in Scheme V.

Scheme (V)

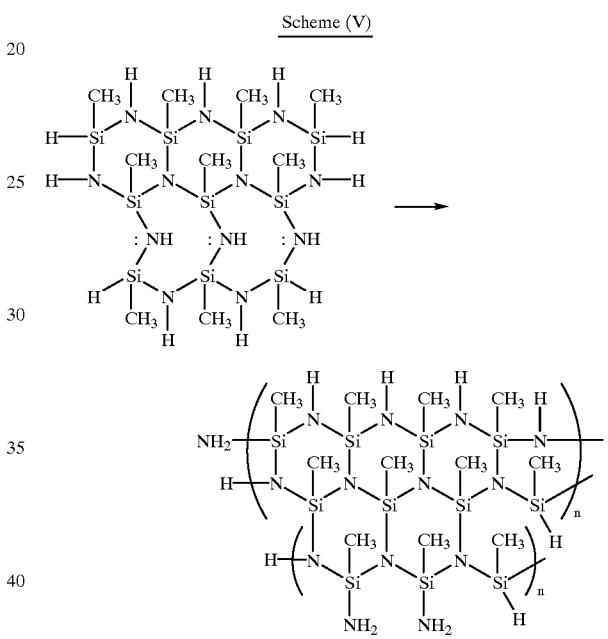

It is theorized that the linear structure from Scheme (I) can also cyclicize forming a small ring in contact with the anhydrous liquid ammonia solution as shown below in Scheme (VI). When the cyclic structure forms it can then react with the ionized ammonium halide salt in the liquid ammonia to attack a Si—N bond for reopening the cyclic structure. The reaction may occur by protonation of the nitrogen atom to generate a cationic species. The chloride counter ion can then attack a silicon atom and a hydride ion migrates to the next silicon in the ring, thereby opening the ring structure. This results in a linear polymer with a chlorine on one end of the chain and a silicon atom on the other end which is substituted with two hydrogen atoms (encircled). This is important in that this silicon end may act as a chain terminator preventing further condensation to a fused cyclic structure at this end of the chain. Having a terminating end on the polymer limits its molecular weight thereby inhibiting the formation of very high molecular weight fused polycyclic polymers that may form intractable compositions.

Scheme (VI)

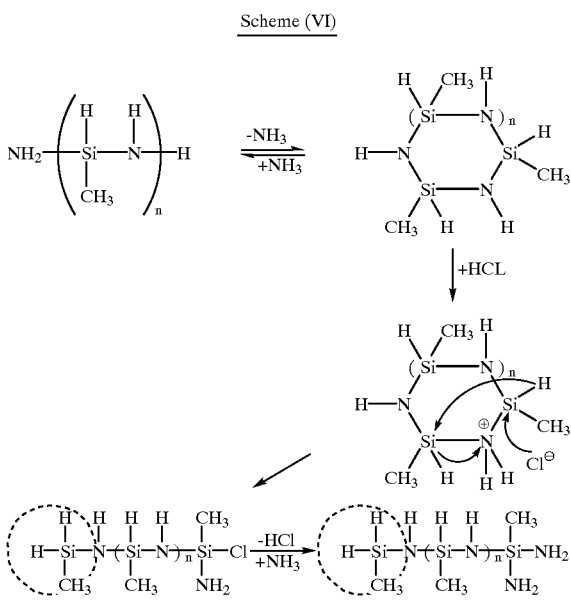

Additionally, dimerization of two linear polymers having end caps can form a distinct four member heterocyclic ring that links islands of ladder like structures together in the final polymer chain as shown in Structure 3. This is a distinct and novel structure in that polymeric chains may extend only from the nitrogen atoms while the silicon atoms remain substituted only with the original organic group or hydrogen atoms. Since it is well know in the art that silazane compounds containing N—H bonds and containing 2 Si—H bonds on the same silicon atom are known to be extremely reactive to self condensation with the evolution of hydrogen gas by-products.

(3)

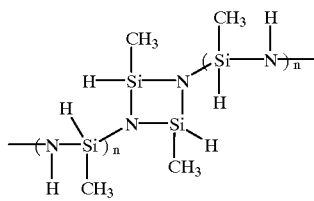

The novel silazanes and/or polysilazanes of the present invention can be prepared by the methods described herein. Specifically, at least one halosilane, preferably having at least one Si—H bond, is introduced into at least twice the stoichiometric amount of liquid anhydrous ammonia relative to silicon-halide bonds, and preferably at least from about five to about ten times. The anhydrous ammonia is maintained at a sufficient temperature and/or pressure to remain liquefied during the process. During the ammonolysis process ammonium halide salt created as a co-product during ammonolysis is retained in the anhydrous liquid ammonia solution. The ammonium halide salt is substantially ionized and solubilized in the anhydrous liquid ammonia, and as such, provides an acidic environment for catalytically preparing the novel silazane and polysilazane compounds of the present invention.

As described above, initially the novel compounds of the present invention may form as linear polysilazane structures which are stabilized against cyclization in the liquid ammonia thereby allowing further ammonolysis reactions to occur on the structure. It is theorized that a Si—H bond in contact with the solubilized and ionized ammonium halide salt, acting as a nonmetallic acid catalyst, is catalytically cleaved by the active ammonium halide salt thereby generating a new silicon-halogen bond on the linear chain of the polymer. The newly generated silicon-halogen bond provides an active site for further ammonolysis. Ammonolysis may continue until all Si—H bonds are cleaved and newly formed silicon-halogen bonds are ammonolysized. Further polymerization may include dimerization of linear polymers to a mixture of four, six, eight or more membered fused cyclic structures.

The viscosity of the novel liquid silazane and/or polysilazane compounds increases as polymerization proceeds. Viscosities of the novel products can be tailored for the preferred end use and can range from about 15 centipoise to a solid material. The increasing viscosity of the polymeric material is dependent upon the length of time the ammonolysis products are retained in the anhydrous liquid ammonia and the initial type and amount of Si—H bond containing starting compounds. Upon completion of the process for preparing the novel silazanes and/or polysilazanes, the products are easily separated from the anhydrous liquid ammonia solution. The novel products are retained in a distinct liquid-phase layer separate from the ammonium halide salts solubilized in the anhydrous liquid ammonia. Furthermore, the novel products require only a limited amount of purification because the ammonium halide salt remains solubilized in the liquid ammonia thereby reducing precipitation of the salt into the prepared product.

In methods of the prior art, an inert solvent must be added to the reaction mixture to overcome the problems associated with precipitating ammonium halide salts which can impede stirring of the reaction mixture. Furthermore, addition of the inert solvent helps to dissipate the heat of crystallization generated by the precipitating ammonium halide salt.

In the methods of the present invention, the addition of an inert solvent is not required because the ammonium halide salt is solubilized in an excess of liquid ammonia instead of precipitating into the novel ammonolysis products. Additionally, the Si—H bond containing starting compounds do not need to be dissolved in an inert solvent before introduction into the anhydrous liquid ammonia thereby eliminating the necessity for separating the solvent from the ammonolysis products.

Although merely a theory it is believed the lack of an inert solvent in the reaction mixture allows silazanes and/or polysilazanes, that may still contain a Si—H bond, to be retained in the ionic and acidic environment for a sufficient time to stabilize to a linear structure for further ammonolysis and/or polymerization. If an organic inert solvent is in the reaction system such as in the methods of the prior art, the nonpolar solvent promotes self-condensation into cyclic structures thereby reducing the formation of linear structures.

In some situations depending on the Si—H bond containing starting compounds, an inert solvent may be used in the methods of the present invention and if so any organic solvent that does not react with the silanes, silazanes, and polysilazanes or interferes and/or participates in the ammonolysis process may be added, including but not limited to benzene, toluene, xylene, pentane, tetrahydrofuran and the like.

To prepare the novel silazane and/or polysilazane compounds according to the present invention, any mono-, di- or tri-halogenated silane may be used. The halosilane utilized as a Si—H bond containing starting compound in the present methods may be selected from the group consisting of $RSiX_3$, $R_2SiX_2$, $R_3SiX$, and mixtures thereof where R may be the same or different, is a hydrogen atom, a lower alkyl group having 1 or more carbons atoms, a substituted or unsubstituted cycloalkyl group having 3 or more carbon atoms, a substituted or unsubstituted lower alkenyl group having 2 or more carbon atoms, or a substituted or unsubstituted lower aryl group having 6 or more carbon atoms, with the proviso that at least one R is a hydrogen atom, and X is a halogen. Specifically, examples of suitable organo-halosilanes include, dichlorosilane, methyl dichlorosilane, dimethyl chlorosilane, diethyl chlorosilane, ethyl dichlorosilane, ethyl dibromosilane, ethyl diiodosilane, ethyl difluorosilane, dichloro monofluorosilane, propyl dibromosilane, iso-propyl dichlorosilane, butyl diiodosilane, n-propyl dichlorosilane, dipropyl chlorosilane, trichlorosilane, n-butyl dichlorosilane, iso-butyl dichlorosilane, iso-amyl dichlorosilane, benzyl dichlorosilane, naphtyl dichlorosilane, propenyl dichlorosilane, phenyl dichlorosilane, diphenyl chlorosilane, methyl ethyl chlorosilane, vinyl methyl chlorosilane, phenyl methyl chlorosilane, dibenzyl chlorosilane, p-chlorophenyl silicon dichloride, n-hexyl dichlorosilane, cyclohexyl dichlorosilane, dicyclohexyl chlorosilane, di-isobutyl chlorosilane, para-tolyl dichlorosilane, di-para-tolyl chlorosilane, para-styryl dichlorosilane, ethynyl dichlorosilane and mixtures thereof.

The selected halosilane or mixtures thereof are introduced directly into and reacted with anhydrous liquid ammonia. Normally during ammonolysis, on a strictly stoichiometric basis, two molecules of ammonia are needed for each halogen atom substituted on a halosilane. One ammonia molecule replaces the halogen atom while the second molecule of ammonia forms an ammonium halide salt. In this regard, it has been found that it is advantageous to introduce the halosilanes into a closable reaction vessel which is already charged with an excess of anhydrous liquid ammonia, preferably, at least twice the amount of ammonia as Si—X bonds present. More preferably, at least five times the amount of ammonia as Si—X bonds.

The halosilane may be introduced into the anhydrous liquid ammonia in a controlled stream, either continuously or periodically, to prevent overheating of the reaction mixture due to the exothermic ammonolysis reaction.

The temperature and/or pressure in the reaction vessel should be within a range to maintain the anhydrous ammonia in a liquefied state. The pressure may range from about 15 psia to about 200 psia. The pressure range will be dependent upon the temperature generated by the reaction, the amount of venting of ammonia during the reaction and whether the reaction vessel is being cooled by an outside cooling source. Accordingly, if the reaction is carried out under ambient pressure then the temperature should be maintained at or below −33° C. Alternatively, if the pressure within the reaction vessel is increased then the temperature may range from above −33° C. to about 130° C. Preferably, the pressure ranges from about 35 psia to about 350 psia with a temperature range from about −15° C. to about 60° C.

Introducing the halosilanes into a stoichiometric excess of liquid anhydrous ammonia relative to the amount of Si—X bonds is very important because the ammonium halide salt formed during the reaction is solubilized in the liquid ammonia phase, and as such, does not precipitate with or into the prepared ammonolysis products but instead remains in a liquid layer distinct from another liquid layer comprising the prepared ammonolysis products. This is in contrast to the processes hitherto known for the manufacture of silazanes wherein precipitated ammonium halide had to be filtered off and the product washed several times to avoid losses. Advantageously, the separation process according to the present invention need not include separating ammonium halide salt from the preferred ammonolysis products.

Additionally, by retaining the ionized ammonium halide salt in the liquid anhydrous ammonia layer the viscosity of the reaction mixture does not increase during the reaction which occurs in the methods of the prior art as levels of precipitated ammonium halide salt increase. The present invention substantially eliminates the formation of a precipitate and this overcomes the need for adding an inert solvent which heretofore in the prior art was added to prevent stalling of the reaction due to the inability to stir the reaction mixture.

Furthermore, while not wishing to be bound by any particular theory of operation, it is believed that by avoiding the precipitation of ammonium halide salts, the resultant exothermic heat of crystallization is not introduced into the reaction vessel thereby substantially eliminating local overheating or temperature peaks and maintaining a more uniform reaction course.

According to the methods of the present invention, the Si—H bond containing starting compounds may be introduced from a secondary pressurized vessel into a primary reaction vessel. The primary vessel is charged with an excess of a stoichiometric amount of anhydrous liquid ammonia, and preferably at least twice the stoichiometric amount based on the number of silicon-halide bonds of the halosilane. A sufficient pressure gradient between the two vessels allows the Si—H bond containing starting compounds to be injected into the primary reaction vessel. Preferably, the pressure gradient is from about 20 psi to about 100 psi, wherein the pressure in the secondary vessel is greater than that of the primary reaction vessel. In the alternative, the starting compounds may be pumped into the vessel.

During the course of the ammonolysis reaction, there may be an increase in temperature in the reaction vessel due to the exothermic reaction. As the temperature increases in the reaction vessel, there may be a tendency for the reaction to overheat and the addition rate may have to be reduced. By reducing the amount of Si—H bond containing starting compound being introduced over a period of time, the heat generated within the vessel may be controlled.

In addition to controlling the input of Si—H bond containing starting compounds into the reaction vessel, the temperature within the vessel and mixture may be maintained by slowly venting a small amount of anhydrous ammonia as a gas. As a consequence, the ammonolysis process may proceed in a timely manner without overheating. Because the length of time to complete the process is greatly reduced, the methods of the present invention are a more cost efficient process for preparing ammonolysis products.

After completion of the ammonolysis process and/or polymerization, the preferred ammonolysis products are easily separated by removing the liquid-phase layer comprising the ammonolysis products from the reaction vessel.

The methods of the present invention may be carried out in both a batch and continuous mode. In either batch or continuous mode, the liquid anhydrous ammonia may become saturated with ionized ammonium halide salt which could initiate the precipitation of salt into the prepared ammonolysis product layer. To avoid this occurrence, some of the liquid ammonia containing the solubilized ammonium halide salt may be removed periodically from the vessel. The solubilized ammonium halide may then be separated from the ammonia by passing through an evaporation chamber wherein the ammonia is evaporated. The evaporated ammonia vapor can be condensed and recirculated into the reaction vessel when needed.

During a continuous process, the ammonolysis products may be withdrawn from their liquid-phase layer. This removal of prepared ammonolysis products may occur after an initial production of a sufficient amount of product to facilitate withdrawal of same from the liquid-phase layer without removing the liquid layer comprising the ammonia and ammonium halide salt.

The novel silazanes and/or polysilazanes of the present invention are useful as fibers, filaments, flakes, powder, films, coatings, and the like, as well as other products such as mats, woven fabric, slabs, sleeves, structural composites, etc. Such shaped articles, because of their chemical composition, represent a material which is oxidation-resistant up to high temperature. Their good physical properties and excellent mechanical strength make them suitable for the lining of parts of apparatuses to be protected against corrosion and oxidation at high temperatures, while foams of such materials can be used very advantageously as temperature-resistant insulating materials. Various shaped articles of silicon nitride such as pipes, crucibles, bricks or the like are suitable for use as high temperature materials because of their good chemical resistance.

In another embodiment of the present invention, the above described method for preparing novel silazanes and/or polysilazanes may also be employed when the reactant is a halogen substituted silane which does not have a Si—H bond. The general procedure of the ammonolysis process disclosed above is applicable thereby providing an easy and cost efficient method to prepare known silazanes and/or polysilazanes. The method to produce known ammonolysis products comprises introducing a halogen substituted silane into liquid anhydrous ammonia. The amount of liquid anhydrous ammonia being at least twice the stoichiometric amount of silicon-halide bonds found on the halogen substituted silane, and more preferably, an excess of anhydrous liquid ammonia. When the halogen substituted silanes are introduced into the anhydrous liquid ammonia, they may be dissolved in an inert solvent, or preferably, be introduced in the absence of an inert solvent.

If an inert solvent is used to dissolve the halogen substituted silanes, then any organic solvent that does not react with the ammonolysis products, interfere with and/or participate in the ammonolysis process may be added including but not limited to benzene, toluene, xylene, pentane, tetrahydrofuran and the like.

To prepare known ammonolysis products according to the methods of the present invention, any halogen substituted silane may be used. Preferably, a mono-, di- or tri-halogenated silane is selected from the group including $RSiX_3$, $R_2SiX_2$, $R_3SiX$, and mixtures thereof, where R may be the same or different from each other and selected from the following group including a hydrogen atom, a substituted or unsubstituted alkyl group, a substituted or unsubstituted cycloalkyl group, a substituted or unsubstituted alkenyl group or a substituted or unsubstituted aryl group, and X is a halogen selected from the group of fluorine, iodine, chlorine and bromine. Tetrafunctional silanes $SiX_4$ may be present as well as halogen substituted disilanes.

The known ammonolysis products formed during the reaction will be dependent upon the starting halogen substituted silane, the number of halogen linkage points, and/or the type of organic groups bound to the silane. Specifically, the known ammonolysis products can include monomers, dimers, linear species, polymers and/or small rings containing at least three or four Si—N units.

For instance, triorganohalosilanes form disilazanes because there is only one halogen linkage point on the silicon atom. Thus understood, when starting with trimethylchlorosilane and injecting same into anhydrous liquid ammonia, hexamethyldisilazane, a dimer, will form during the condensation reaction such as shown below.

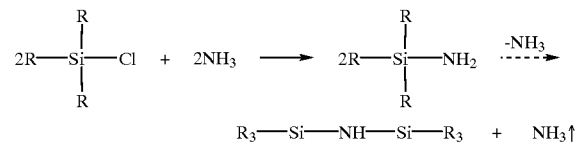

It has been found that it is advantageous to introduce the halosilanes into a closable reaction vessel which is already charged with anhydrous liquid ammonia in an amount at least twice the stoichiometric amount of silicon-halide bonds, and preferably, at least five times the amount of silicon-halide bonds. The halogen substituted silane is introduced in a controlled stream, either continuously or periodically, to prevent overheating of the reaction mixture due to the exothermic ammonolysis reaction. Pressure and temperature conditions of the reaction system are the same as that described above.

Introducing the halosilanes directly into a stoichiometric excess of liquid anhydrous ammonia is very important because the ammonium halide salt formed during the reaction is solubilized in the liquid ammonia phase, and as such, does not precipitate with or into the prepared ammonolysis products. In contrast to the processes hitherto known for the manufacture of silazanes wherein precipitated ammonium halide had to be filtered off and the product washed several times to avoid losses, the separation according to the present invention need not include separating ammonium halide salt from the preferred ammonolysis products.

As described above, by retaining the ionized ammonium halide salt in the liquid anhydrous ammonia layer the viscosity of the reaction mixture does not increase during the reaction thereby eliminating the need for inert solvents which heretofore were added to prevent stalling of agitation of the reaction mixture.

Upon completion of the process, the products are easily separated from the anhydrous liquid ammonia solution. The ammonolysis products are retained in a distinct liquid-phase layer separate from the ammonium halide salts solubilized in the anhydrous liquid ammonia. By theory this separation is facilitated by the ionic environment of the anhydrous liquid ammonia due to the solubilized ammonium halide salts.

The ammonolysis products require a limited amount of purification due to the fact that the ammonium halide salt is solubilized in the liquid ammonia thereby reducing precipitation of the salt and contamination of the final ammonolysis products. Additionally, solubilization of the ammonium halide salt ameliorates the heat of crystallization of the salt which is a problem found in the prior art.

Still another embodiment of the present invention provides for further polymerization and/or structural rearrangement of silazanes and/or polysilazanes whether prepared by the methods described herein or by methods of the prior art. Several methods of the prior art produce low molecular weight species which can evaporate during pyrolysis thereby reducing the weight yield of ceramic product relative to the starting material. In addition, many polysilazanes are not heat-stable during pyrolysis because the structural silicon-nitrogen bonds are broken during pyrolysis causing some polysilazanes to decompose into volatile oligomers which further reduces the weight of ceramic material.

To overcome the above problems, the present invention provides a method to modify known silazane and/or polysilazane compounds as well as novel silazanes and/or polysilazanes disclosed herein by preparing a polysilazane of higher molecular weight and/or increasing viscosity. The method comprises introducing a silazane and/or polysilazane having at least one Si—H bond into a solution of anhydrous liquid ammonia containing a catalytically effective amount of a solubilized and/or ionized acid catalyst in the anhydrous liquid ammonia.

The anhydrous liquid ammonia is maintained at a sufficient temperature and pressure to maintain the anhydrous ammonia in a liquefied state, as described above. Preferably, the silazanes and/or polysilazanes having at least one Si—H bond are retained in the anhydrous liquid ammonia and in contact with the acid catalyst ionized therein for a time sufficient to polymerize and/or co-polymerize and/or structurally rearrange the silazanes and/or polysilazanes.

The acid catalyst may be any nonmetallic acid or salt thereof that can be solubilized and/or ionized in anhydrous liquid ammonia, including, but not limited to inorganic salts, such as ammonium salts including ammonium halide and ammonium nitrate; and organic salts, such as ammonium acetate, or a mixture thereof. Generally only small amounts of the acid catalyst are necessary, such as 0.1–10 mole percent based on the Si—H bonds in the starting silazanes and/or polysilazanes because the reaction is catalytic.

While not wishing to be bound by any particular theory of operation, it is believed that the Si—H bond of the silazane and/or polysilazane compounds in contact the anhydrous liquid ammonia, containing the solubilized and ionized acid catalyst, is catalytically cleaved and halogenated to generate an active site for further ammonolysis. Ammonolysis may continue until all Si—H bonds are cleaved and newly formed active sites are ammonolysized. Further polymerization may contain cyclic structures, such as at least four membered rings, fused cyclic structures, linear structures and a mixture thereof.

The modified silazane and/or polysilazane compounds can be separated from the reaction mixture by any separation method known to those skilled in the art. Separation of the modified polysilazanes is easily effected because the modified polysilazanes separate into a distinct liquid layer away from the liquid ammonia containing the ionized acid catalyst. Preferably, the liquid ammonia containing the acid catalyst is removed from the system, such as by draining or decanting, leaving the modified products.

Although use of the methods disclosed herein provide silazanes and/or polysilazanes that are essentially free of the unwanted co-products such as precipitated ammonium halide salts, the methods disclosed in the prior art usually require extensive filtration and purification of the ammonolysis products.

Unexpectedly, it has been discovered by the inventors that removal of unwanted by-products, such as ammonium halide salts from prepared ammonolysis products can be accomplished by introducing known silazanes and/or polysilazanes as well as the novel silazanes and/or polysilazanes disclosed herein, containing these salts, into a sufficient amount of anhydrous liquid ammonia to solubilize and/or ionize the ammonium halide salt. The silazanes and/or polysilazanes are retained and agitated in the anhydrous liquid ammonia until the ammonium halide salts are solubilized and ionized therein. The purified silazanes and/or polysilazanes separate into a distinct liquid layer away from the ionized ammonium halide salts retained in the anhydrous liquid ammonia.

In an alternative method of purification, an alkali or alkaline earth metal is added to the anhydrous liquid ammonia, which contains prepared silazanes and/or polysilazanes and ammonium halide salt, in a sufficient stoichiometric amount relative to the amount of ammonium halide dissolved in the anhydrous liquid ammonia to prepare an alkali or alkaline earth metal halide salt. The alkali or alkaline earth metal halide salt is essentially neutral and as such will not react further with the silazane and/or polysilazane products.

The dissolution of an alkali or alkaline earth metal, such as sodium, in the anhydrous liquid ammonia generates the necessary alkali or alkaline earth cations along with solvated electrons. Largely for reasons of availability and economy, it is most preferred that the alkali or alkaline earth metal be selected from the group consisting of Li, Na, K, Ca, and mixtures thereof. In most cases, the use of sodium, which is widely available and inexpensive, will prove to be satisfactory.

In the present invention, the alkali or alkaline earth metal may be introduced into the anhydrous liquid ammonia under stirring conditions at a controlled rate to facilitate dissolution of metal. The amount of metal introduced into the reaction vessel should be in a sufficient amount to generate a stoichiometric amount of cations and solvated electrons to react and/or combine with ammonium ions ionized in the anhydrous liquid ammonia and in an amount not exceeding the solubility of the metal in anhydrous liquid ammonia.

Alternatively, the active metal may be predissolved in anhydrous liquid ammonia before the contaminated ammonolysis products are introduced into the liquid ammonia.

For purposes of explanation, sodium will be used as a representative of an alkali metal but this is not intended to be a limitation of the invention. When sodium and other alkali or alkaline earth metals dissolve in an ammoniacal liquid, such as liquid ammonia, cations and solvated electrons are chemically generated. The sodium becomes a cation by losing a valence electron as illustrated in the following equation:

The solvated electrons react with ammonium ions, neutralizing them and forming hydrogen gas as shown below:

The sodium cations are free to combine with a halide anion in solution forming a neutral alkali metal or alkaline earth metal salt.

The neutral alkali metal or alkaline earth metal salt can be removed from the silazanes and/or polysilazanes by any means of separation known in the art including filtration.

Unexpectedly, it has been discovered by the inventors that the addition of an alkali or alkaline earth metal provides a mechanism for solidifying a liquid ammonolysis product. In the solidification process, liquid novel and known silazanes and/or polysilazanes, with and/or without Si—H bonds, whether prepared by methods of the present invention or methods disclosed in the prior art, are introduced into a sufficient amount of anhydrous liquid ammonia to disperse and/or dissolve the silazanes and/or polysilazanes in a homogenous phase. A catalytic amount of alkali or alkaline earth metal is added to this solution. The amount of the metal must be at least as great as that which is necessary to neutralize any ammonium halide salt remaining in the silazanes and/or polysilazanes, and preferably, ranging from about 0.1 to about 10 mole percent based upon the NH containing repeat units in the starting silazanes and/or polysilazanes because the reaction is catalytic.

With the addition of an alkali or alkaline earth metal in the anhydrous liquid ammonia, the typical blue color is produced in the ammonia solution indicating the production of solvated electrons and metal cations. The blue color within the solution disappears as the solvated electrons are consumed within the reaction mixture to initiate the solidification process.

The solidification process can be interrupted by quenching the reaction with the addition of an acidic reagent, preferably, an ammonium salt, and more preferably, an ammonium halide. This quenching at specific times into the solidification process provides for a range of products having controllably increasing viscosities ranging from low to very high viscosity dependent upon reaction time and point of quenching.

The invention will now be described in more detail in the following examples which serve merely to explain the invention and should in no way limit the scope of the protection of the invention.

EXAMPLE 1

Ammonolysis of Methyldichlorosilane Using the Methods of the Present Invention

A 6 liter pressure reactor was charged with 2.5 liters of commercial grade anhydrous liquid ammonia. The ammonia was transferred directly from a bulk cylinder without additional purification. The pressure reactor was equipped with a thermometer and pressure gauge. For mixing, a pump around loop withdrew liquid from the bottom of the reactor and injected into the upper portion of the reactor below the liquid ammonia surface.

Methyldichlorosilane (237.2 g, 2.06 moles) was stored in a glass pressure tube under a nitrogen blanket maintained at 100 psia, a pressure greater than the anticipated pressure of the reactor.

Ammonia was vented from the reactor to cool the system to −6° F. The methyldichlorosilane was added in portions to the reactor. The addition was continued until the reaction exotherm caused the pressure in the reactor to increase to a predetermined maximum (about 70 psia). The addition of methyldichlorosilane was then stopped, and the reactor was cooled by venting ammonia. When the reactor reached about 20° F. the addition of methyldichlorosilane was resumed. Continuing this sequence of methyldichlorosilane addition and autorefrigeration, the methyldichlorosilane was added over a 14 minute period.

The reaction of methyldichlorosilane and ammonia was very rapid; as soon as the methyldichlorosilane addition commenced the temperature (and hence the pressure) in the reactor began to rise. When the flow of methyldichlorosilane was stopped the temperature and pressure rise also stopped simultaneously. Any ammonium chloride salt that was generated was solubilized in the anhydrous liquid ammonia.

After completion of the silazane and/or polysilazane synthesis the reactor contained a two-phase system. One layer consisted of liquid ammonia with the dissolved ammonium chloride salt therein and the other layer contained the ammonolysis products. The layers were easily separated.

COMPARATIVE EXAMPLE 2

As a comparison representing the state of the prior art, silazanes were prepared by introducing ammonia gas into a kettle containing an inert solvent with halosilanes dissolved therein. The procedure was as follows:

A two-liter resin kettle was equipped with a stirrer, thermometer and a dry ice/isopropyl alcohol condenser. 416 grams (608 ml) of heptane was added to the reactor. Methyldichlorosilane (55.25 g, 0.48 moles) was added and then followed by the addition of methylvinyldichlorosilane (16.86 g, 0.12 moles). The mixture was stirred and cooled by an ice bath to around 20° C.

Ammonia vapor was added to the reactor at a slow rate to maintain the temperature at about 20° C. As soon as the ammonia flow began, the vapor space in the reactor was filled with a white fog and the heptane solvent contained a white suspension of ammonium chloride salt.

The ammonia (62.1 g, 3.65 moles) was added over a period of 3 hours and 55 minutes. The time for introducing the ammonia into the reaction vessel took an extended time because the ammonia must be added at a slow pace to allow stirring of the reaction mixture without causing a rapid buildup of ammonium halide salt and to maintain the operating temperature of approximately 20° C. The suspension of ammonium chloride salt in the heptane solution was quite thick but efficient stirring was maintained throughout the ammonia addition.

After completion of the ammonolysis process the ammonium chloride salt was removed from the solvent slurry by filtration. The ammonolysis products were isolated by distillation of the heptane solvent. The yield of ammonium chloride was 56 g, (87% of theory), the yield of ammonolysis products was 27.9 g, (72% of theory).

The results of the comparative study show important differences in the effectiveness of the method of the present invention over the methods of the prior art. Specifically, the methods of the prior art which add gaseous ammonia to a mixture of halosilane dissolved in inert solvent took almost four hours for the ammonolysis process that only reacted 70 grams of halosilanes and required extensive filtration and isolation to separate and purify the product. In contrast, the methods of the present invention completed ammonolysis of almost 250 grams of the halosilane within 15 minutes. The ammonolysis products synthesized by the present invention required no further purification to isolate the desired products because separation was facilitated by distinct liquid layers that isolated the ammonolysis products away from any unwanted salt by-products.

EXAMPLE 3

Preparation and Polymerization of Tetramethyldisilazane Using the Methods of the Present Invention A 6 liter pressure reactor was charged with 4.0 liters of commercial grade chilled (−30°) anhydrous liquid ammonia. Approximately 1 kg. (7.5 moles) of dimethylchlorosilane was added to an addition tank which was pressurized to approximately 160 psia by nitrogen gas. The dimethylchlorosilane was added to the anhydrous liquid ammonia by the pressure difference in the two tanks. After about one half of the halosilane was introduced into the anhydrous liquid ammonia, the reactor tank was vented to reduce the pressure and further chill the system. The remainder of the halosilane was introduced to complete the addition in approximately 30 minutes. The reaction vessel was stirred for about 10 minutes and then agitation was discontinued. The reaction mixture spontaneously separated into two distinct layers. A sample was taken from the upper layer and any dissolved ammonia was evaporated. The clear sample was analyzed by Fourier Transform Infrared (FTIR) Spectroscopy and shown to be tetramethyldisilazane when compared to an authentic spectrum. Stirring was resumed and additional samples were taken as outlined in the following Table 1.

TABLE 1

| Sample | Time | Reactor Pressure | Reactor Temperature | Reaction Time |
| --- | --- | --- | --- | --- |
| 1 | 10:20 am | 120 psi | 21.7° C. | 30 min. |
| 2 | 10:50 am | 100 psi | 19.6° C. | 1.0 hr |
| 3 | 11:20 am | 104 psi | 20.6° C. | 1.5 hr |
| 4 | 1:20 pm | 124 psi | 25.5° C. | 3.5 hr |
| 5 | 2:20 pm | 129 psi | 26.0° C. | 4.5 hr |
| 6 | 4:20 pm | 131 psi | 25.4° C. | 6.5 hr |
| 7 | 10:20 am | 139 psi | 21.3° C. | 24 hrs |
| 8 | 2:20 pm | 154 psi | 23.8° C. | 28 hrs |
| 9 | 4:20 pm | 155 psi | 24.0° C. | 30 hrs |
| 10 | 9:20 am | 148 psi | 21.4° C. | 47 hrs |

Results:

Initially it should be recognized that during the reaction process there was a continuous increase in pressure indicating that an ongoing reaction was occurring. All samples were analyzed by FTIR. After all spectra were normalized changes in the spectra became evident. FIG. 1 illustrates the changes in several areas of the spectra during the course of the reaction from t=0.5 hrs (dotted line) to t=47 hrs (full line). It is evident that the number of Si—H bonds decreased during the reaction as shown by the intensity of Si—H peaks at ≈879 cm$^{-1}$ (FIG. 1(c)) and 2115 cm$^{-1}$ (FIG. 1(a)). Additionally, a peak at ≈1174 cm$^{-1}$ (FIG. 1(b)) relates to an increasing Si—N character. These changes are concomitant with the process of polymerization wherein Si—H bonds are cleaved allowing further ammonolysis with an increase in Si—N functionality. The results indicate that additional Si—N linkages occurred at the cleaved Si—H bond sites leading to polymers having an increased number of Si—N units.

EXAMPLE 4

Further Polymerization of Methylhydridomethylvinylpolysilazane, a Known Silazane A sample of methylhydridomethylvinylpolysilazane, having an available Si—H bond as shown by the structure below, where R is methyvinyl, was prepared by methods of the prior art as outlined in Example 2.

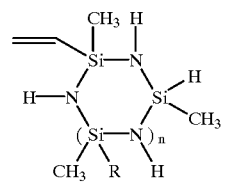

Figure 2:
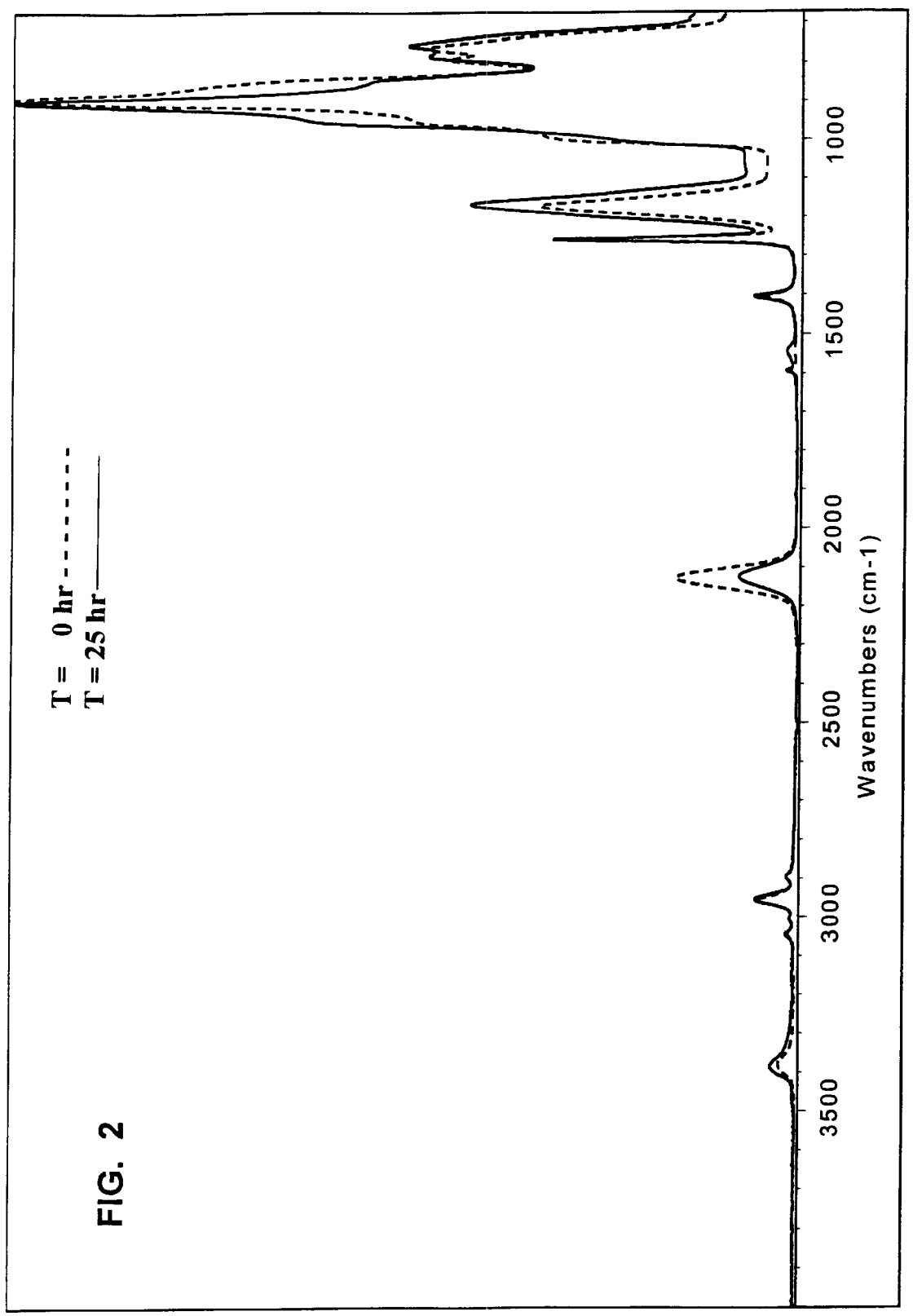
FIG. 2 graphically represents the FTIR spectra of further polymerization of methylhydridomethylvinylpolysilazane prepared by methods of the prior art.

The prepared sample was introduced into a mixture of anhydrous liquid ammonia and a catalytic amount of NH$_4$Cl to effect further polymerization of the sample. FIG. 2 represent the comparative FTIR spectra of the methylhydridomethylvinylpolysilazane before polymerization treatment and after 25 hours of treatment. Viewing FIG. 2 at ≈1500 cm$^{-1}$ at time zero (dotted line), it is evident that initially the methylhydridomethylvinylpolysilazane has limited amine (NH$_2$) functionality at ≈1500 cm$^{-1}$. After 25 hours in the liquid ammonia solution (full line) containing an ionized acid catalyst there was a marked increase in the amine functionality at ≈1500 cm$^{-1}$, a decrease in Si—H bonds as shown at ≈2120 cm$^{-1}$, and a decrease in cyclic character at ≈820 cm$^{-1}$ with an increase in an Si—NH character at ≈1170 cm$^{-1}$.

The results of the polymerization reaction show an increase in Si—N bonds which is proportional to a decrease of cyclic molecules and cleavage of Si—H bonds. It is theorized that rings were opened and stabilized in the acidic environment of the anhydrous liquid ammonia, caused by the solubilized ammonium halide salt, and further polymerization occurred at the Si—H bond sites after cleavage.

EXAMPLE 5

Ammonolysis of Methyldichlorosilane and Vinylmethyldichlorosilane and Further Polymerization Using the Methods of the Present Invention Using the same general procedure of the present invention as outlined in Example 1, a polysilazane was prepared using 80% of methyldichlorosilane and 20% of vinylmethyldichlorosilane. Samples of the ammonolysis products were withdrawn during the process to examine the catalytic formation of extended polymers as shown below in Table 2.

TABLE 2

| Sample | 1 | 2 | 3 | 4 | 5 | 6 |
| --- | --- | --- | --- | --- | --- | --- |
| Time | 2.5 hrs | 6.5 hrs | 12 hrs | 72 hrs | 106 hrs | 130 hrs |

Figure 3:
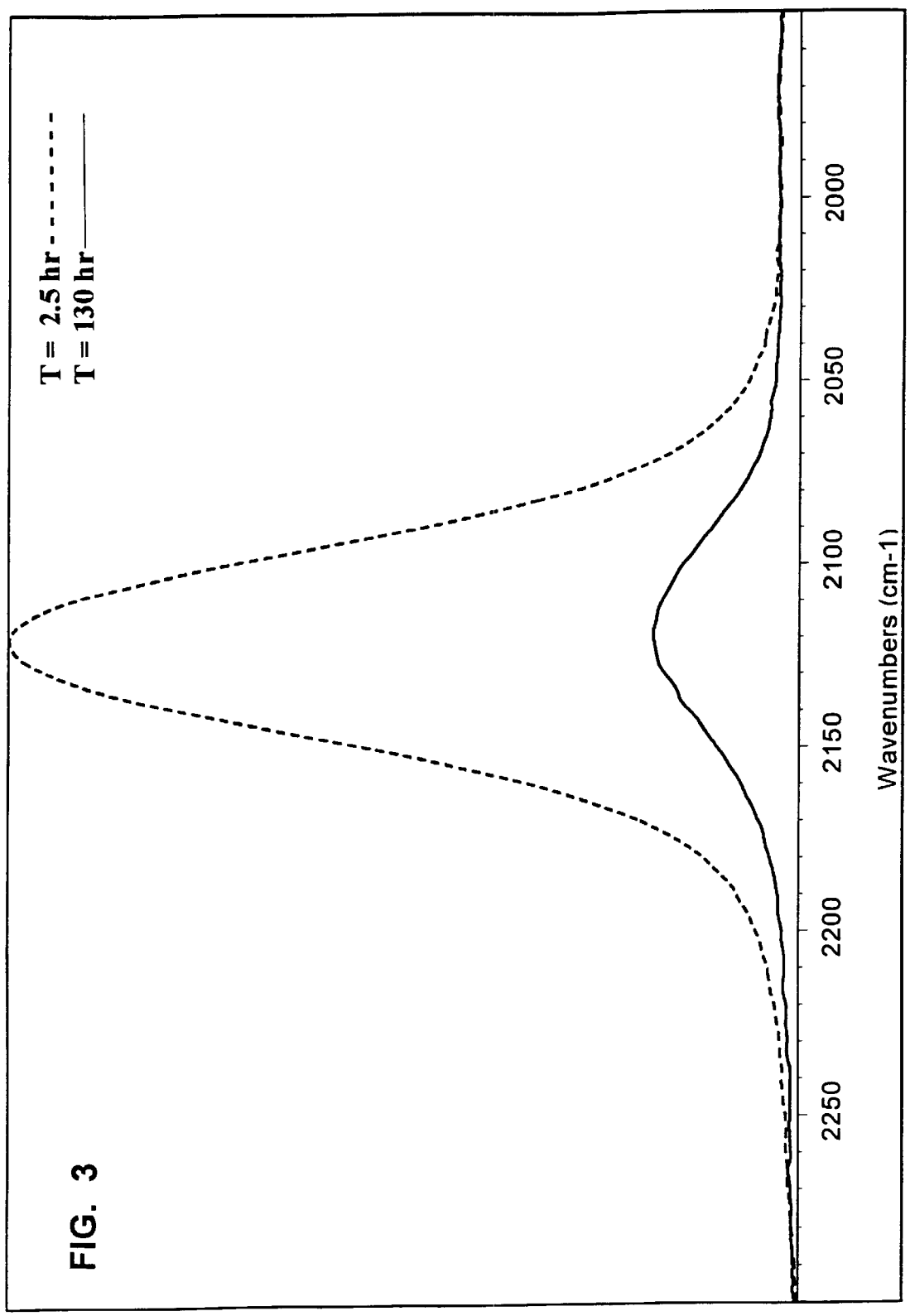
FIG. 3 graphically represents the FTIR spectra of methylhydridomethylvinylpolysilazane prepared according to the methods of the present invention showing a reduction of Si—H functionality over time of the reaction.
Figure 4:
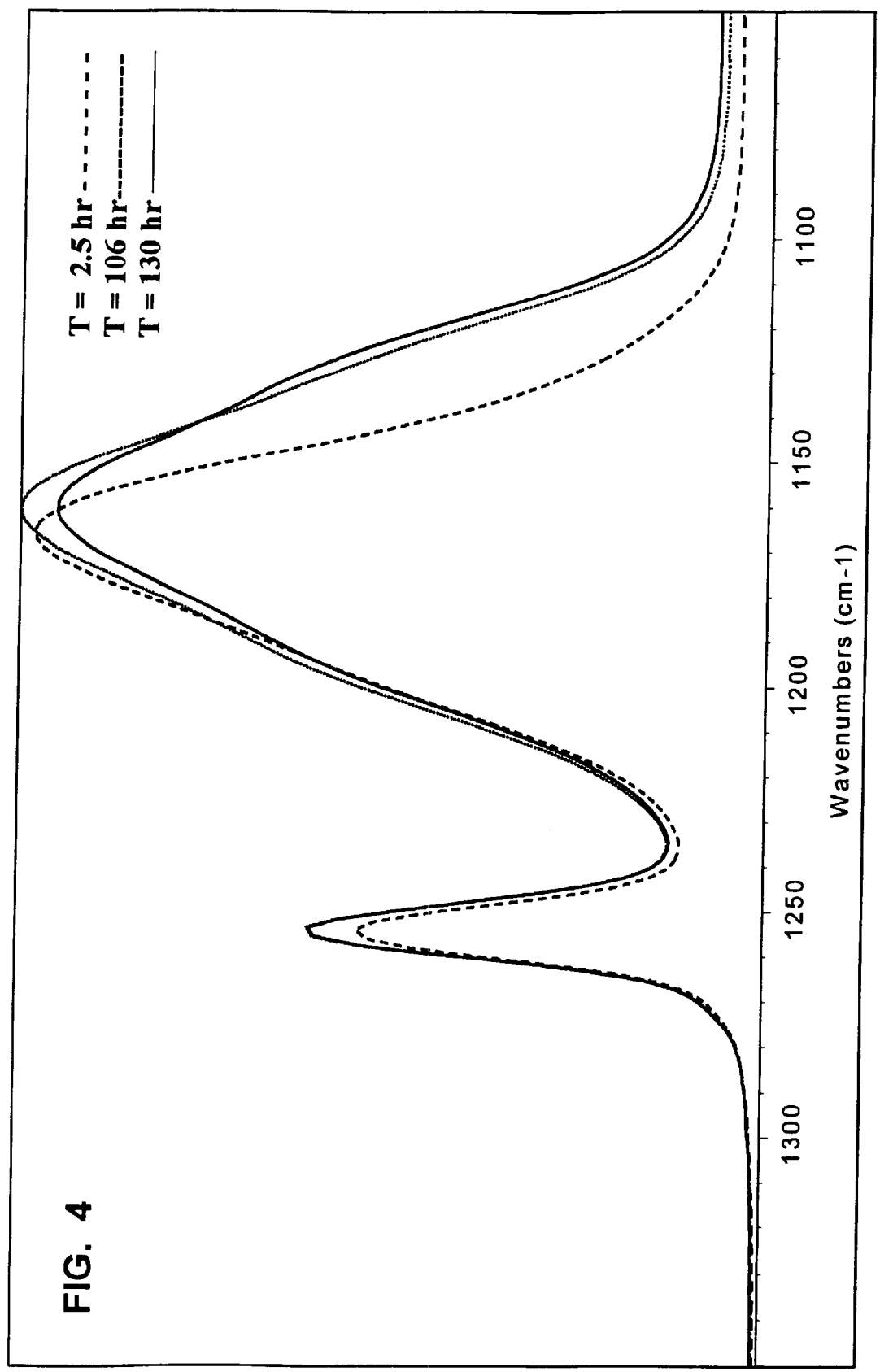
FIG. 4 graphically represents the FTIR spectra of the silazane of FIG. 3 showing the overall change in amine character of the polymer during the process.
Figure 5:
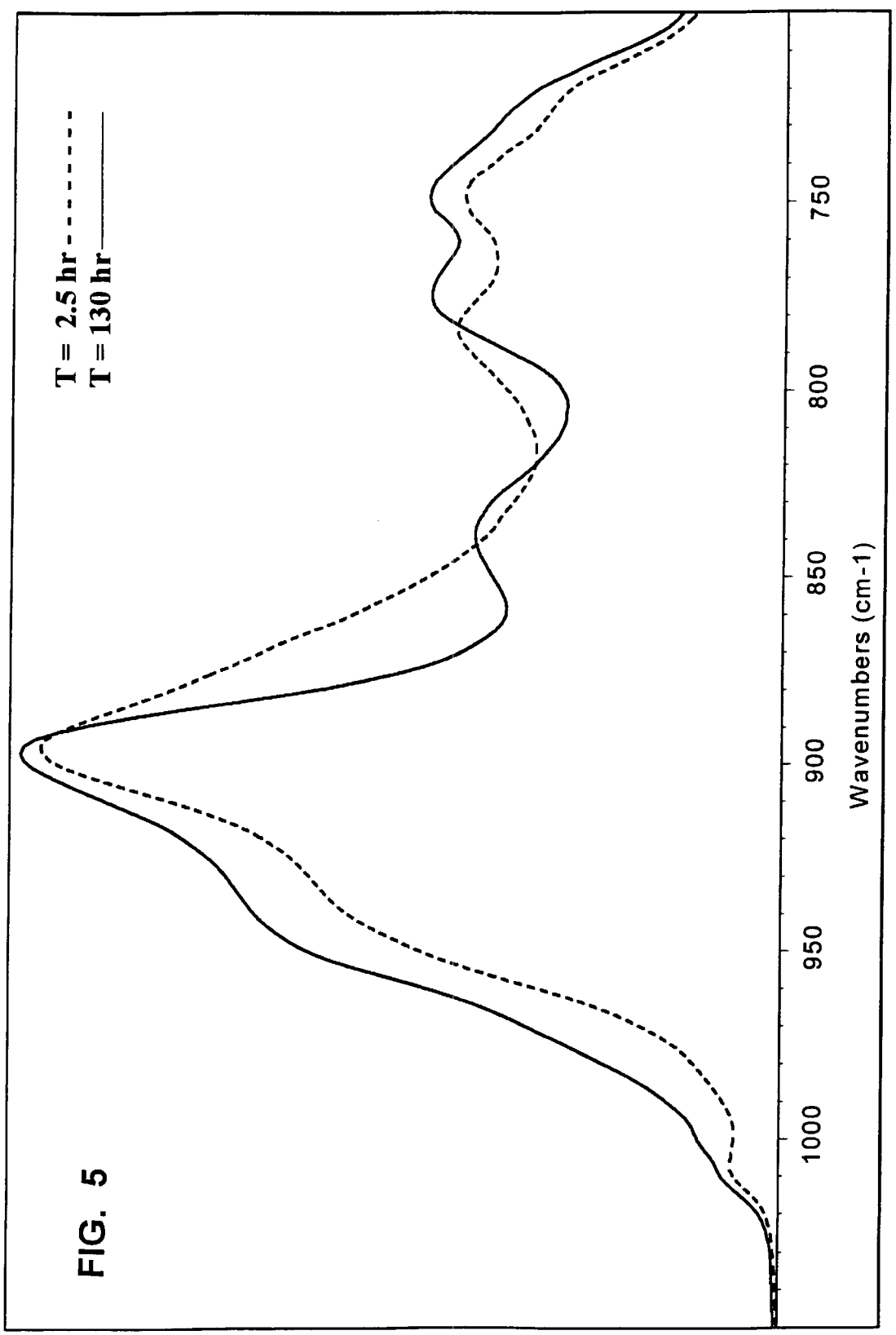
FIG. 5 graphically represents the FTIR spectra of the silazane of FIG. 3 showing the progressive evolution from a linear to condensed structures.

FIGS. 3, 4, and 5 provide graphic representations of the conversion to an extended polymer during the testing period. Specifically, FIG. 3 represents the change in the number of Si—H bonds over time from t=2.5 hrs (dotted line) to t=130 hrs at approximately 2120 cm$^{-1}$ which indicates the overall reduction of Si—H bonds. FIG. 4 shows the overall change in the amine (NH) character of the polymer during the process which increases greatly from t=2.5 hrs to t=130 hrs as indicated by the peak shown at approximately 1170 cm$^{-1}$. FIG. 5 represents the progressive evolution of the polymer from linear structures to condensed fused ring structures.

The results indicate that further polymerization occurred at the cleaved Si—H bond sites leading to increased Si—NH bonds and further linkages between Si—N units.

EXAMPLE 6

Comparison of The Methylvinylmethylhydridopolysilazane Produced by Methods of Present Invention and Prior Art Using the same general procedure of the present invention as outlined in Example 1 a novel polysilazane was prepared using 80% of methyldichlorosilane, having an Si—H bond, and 20% of vinylmethyldichlorosilane and defined as Product 1.

The process for preparing novel compounds of the present invention provides an acidic and ionic environment wherein the ammonolysis products are retained. This facilitates the close contact of an ammonolysis product with an effective catalyst to catalytically cleave Si—H bonds and allow for continued ammonolysis to increase Si—N linkages in the final product.

Using the methods of the prior art as outlined in Example 2 a known polysilazane was prepared using 80% of methyldichlorosilane and 20% of vinylmethyldichlorosilane, dissolved in an inert organic solvent and defined as Product 2. During the ammonolysis process the formed silazane compounds are intermixed with an ammonium halide salt precipitate, and thus, there is no acidic and/or ionic environment formed by an ionized ammonium salt ionized in liquid ammonia. Instead, the formed silazanes migrated and/or remained in the organic medium upon formation.

Figure 6:
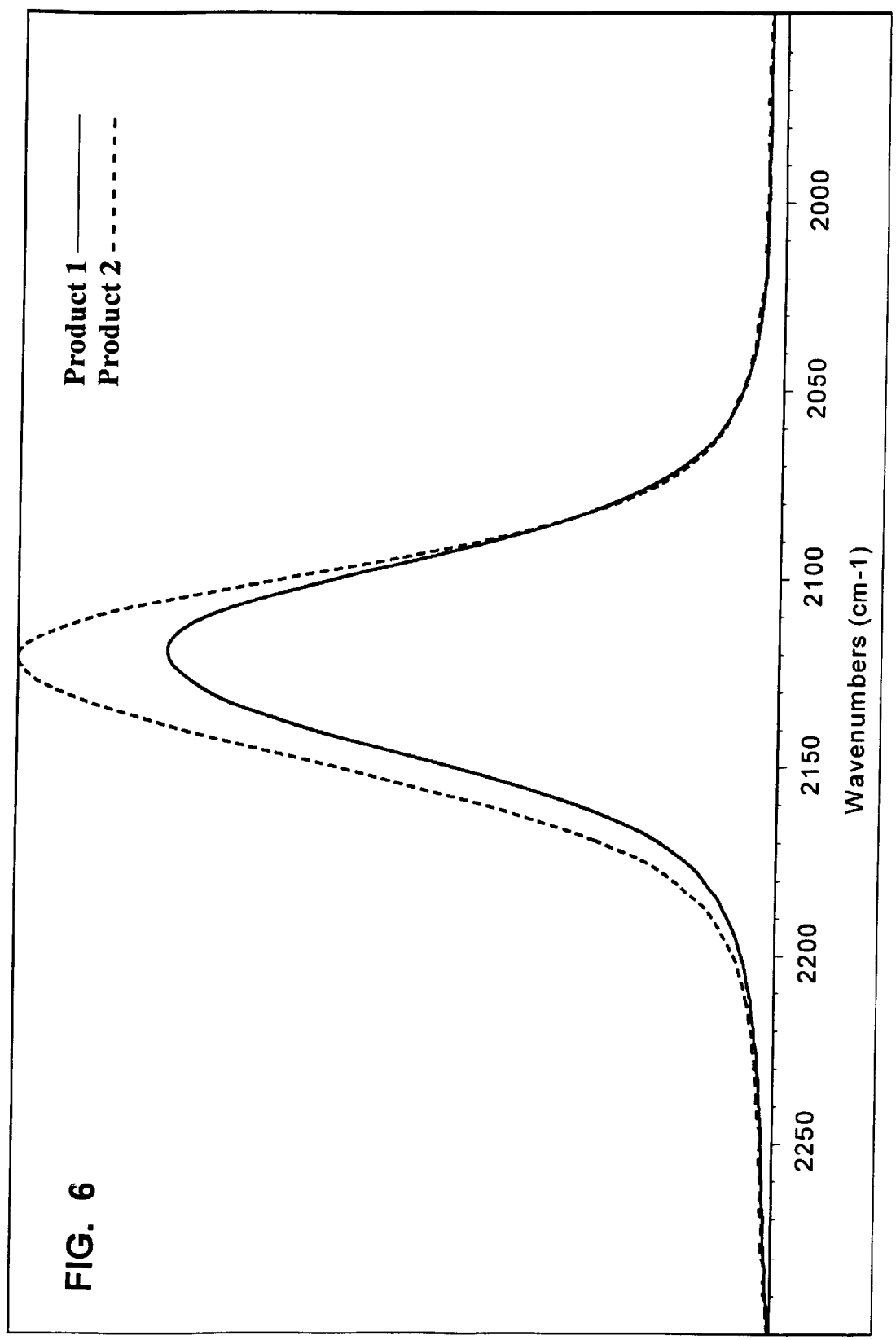
FIGS. 6 and 7 graphically represent the FTIR spectra of the initial product of methylhydridomethylvinylpolysilazane prepared according to the methods of the present invention (Product 1) and methods of the prior art (Product 2).
Figure 7:
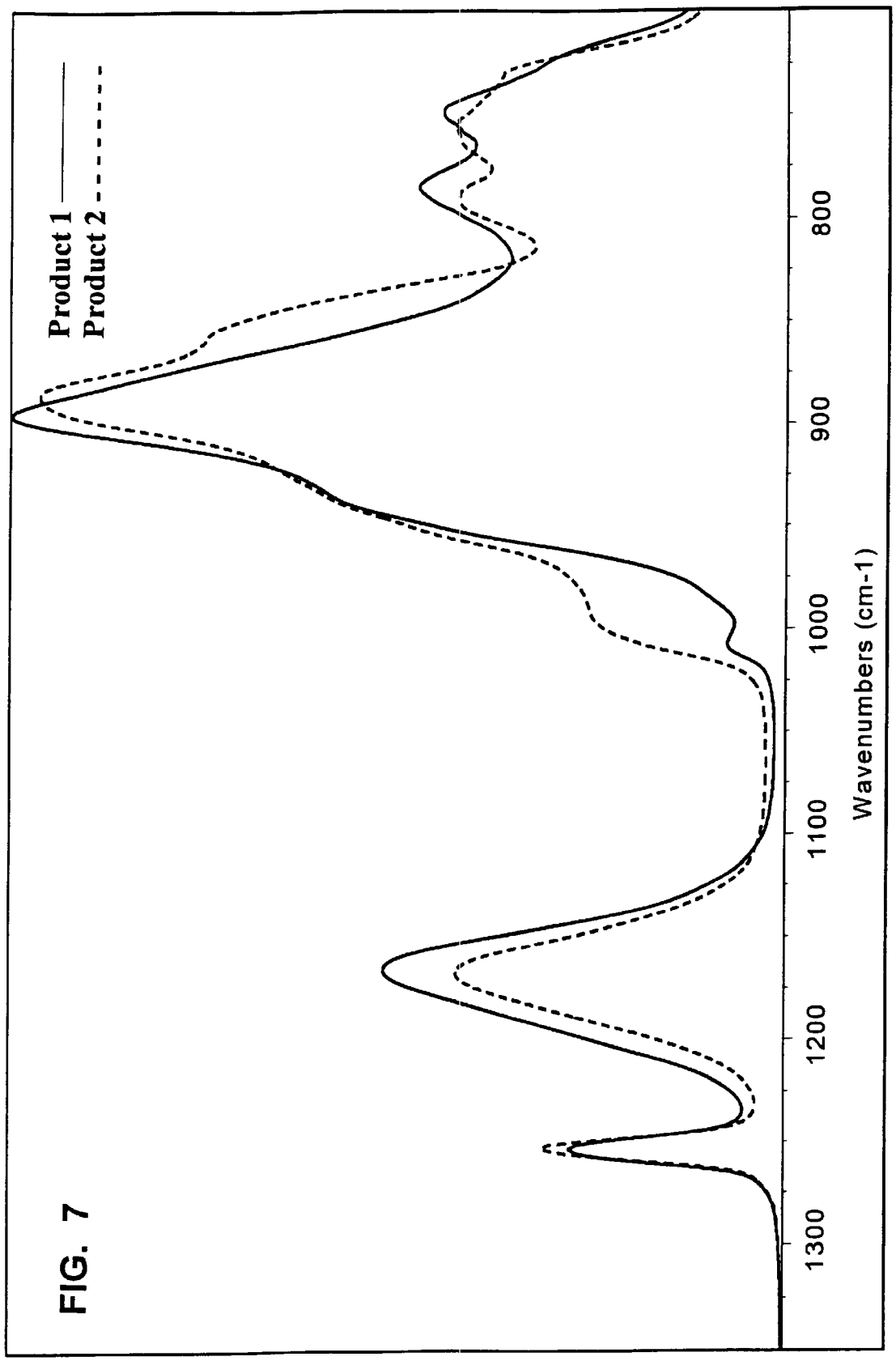

FIGS. 6, and 7, show FTIR spectra of Product 1 and 2 at time zero (t=0), that being when all materials were introduced into the reaction system. Product 1, the novel product of the present invention, formed by the addition of halosilane into an excess of anhydrous liquid ammonia was completed in less than one hour, at which time the spectrum was generated. Product 2, the product prepared according to the methods of the prior art, took approximately one and a half hours to add the gaseous ammonia to the reaction system. The extended time of delivery of the gaseous ammonia was due to the difficulties which were encountered with the formation of large quantities of precipitated ammonium chloride, as well as the generation of excessive heat when gaseous ammonia is added too quickly. After all the reactants were combined the initial spectrum was generated.

In FIG. 6 it is clearly shown that Product 1 (full line) has a decreased amount of Si—H functionality at approximately 2120 cm$^{-1}$ when compared to Product 2 (dotted line) indicating that the Si—H bonds readily react in the acidic environment used in the methods of the present invention. Additionally, the Si—NH environment shown at ≈1170 cm$^{-1}$ in FIG. 7 was greater in Product 1 when compared to that of Product 2. Also shown in FIG. 7 at ≈900 cm$^{-1}$ is the greater linear character of Product 1 in comparison to the cyclic character of Product 2 shown at approximately 850 cm$^{-1}$. Product 1 has increased signal intensity at ≈900 cm$^{-1}$ as well as a narrower signal indicating a more uniform polymer system.

It is evident that formation of the novel silazanes and polysilazanes occurs immediately upon addition of the halosilanes into an excess of anhydrous liquid ammonia. The increased Si—NH functionality at 1170 cm$^{-1}$ indicates more Si—NH character is present in the novel compounds of the present invention. It is believed that the increased Si—NH character is more likely to be present as linear polymer chains as shown by the increase in linear character at ≈900 cm$^{-1}$.

Figure 8:
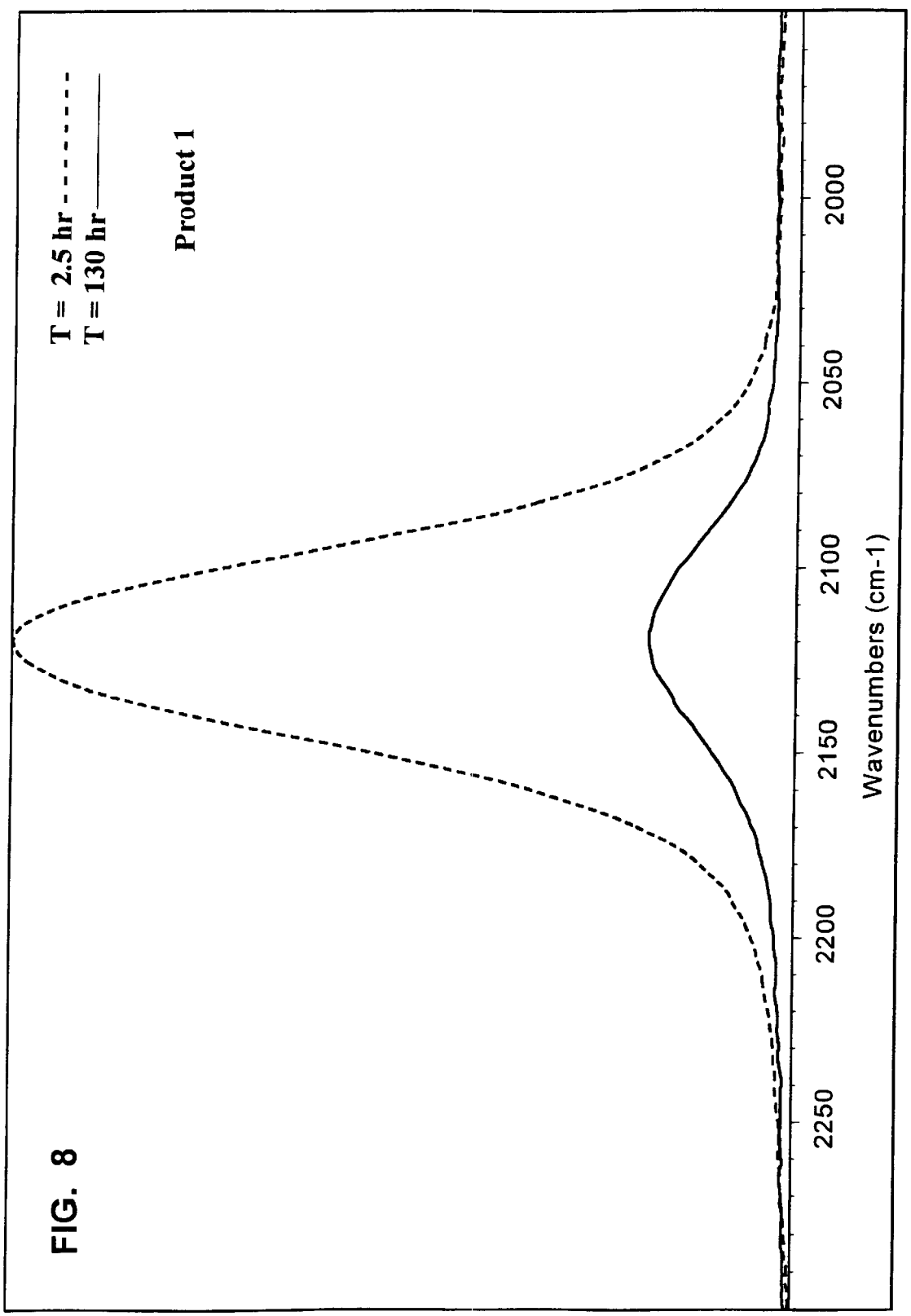
FIGS. 8 and 9 graphically represent the FTIR spectra of Product 1 at t=2.5 and t=130 hours into the polymerization process.
Figure 9:
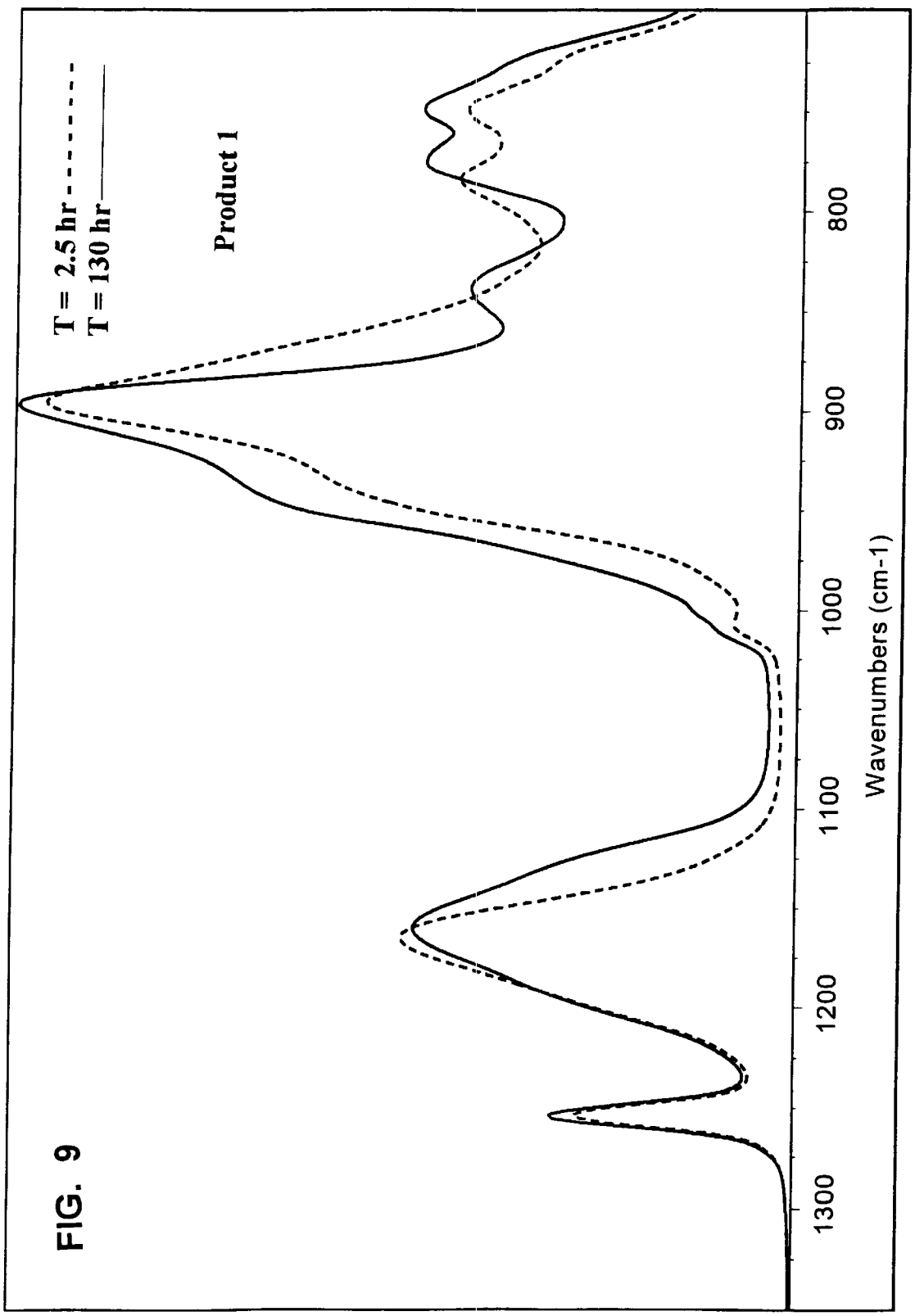

FIGS. 8 and 9 provide further information on Product 1 after 130 hours in the reaction system of the present invention. FIG. 8 shows that during the time from 2.5 hrs to 130 hours there was a marked reduction in Si—H bonds in Product 1, as shown in the decrease of the peak at approximately 2120 cm$^{-1}$.

Similarly, in FIG. 9 the Si—NH functionality at approximately 1170 cm$^{-1}$ is broadened and shifted to the right indicating a dramatic change in the Si—NH and Si—N bonds environment over time.

Figure 10:
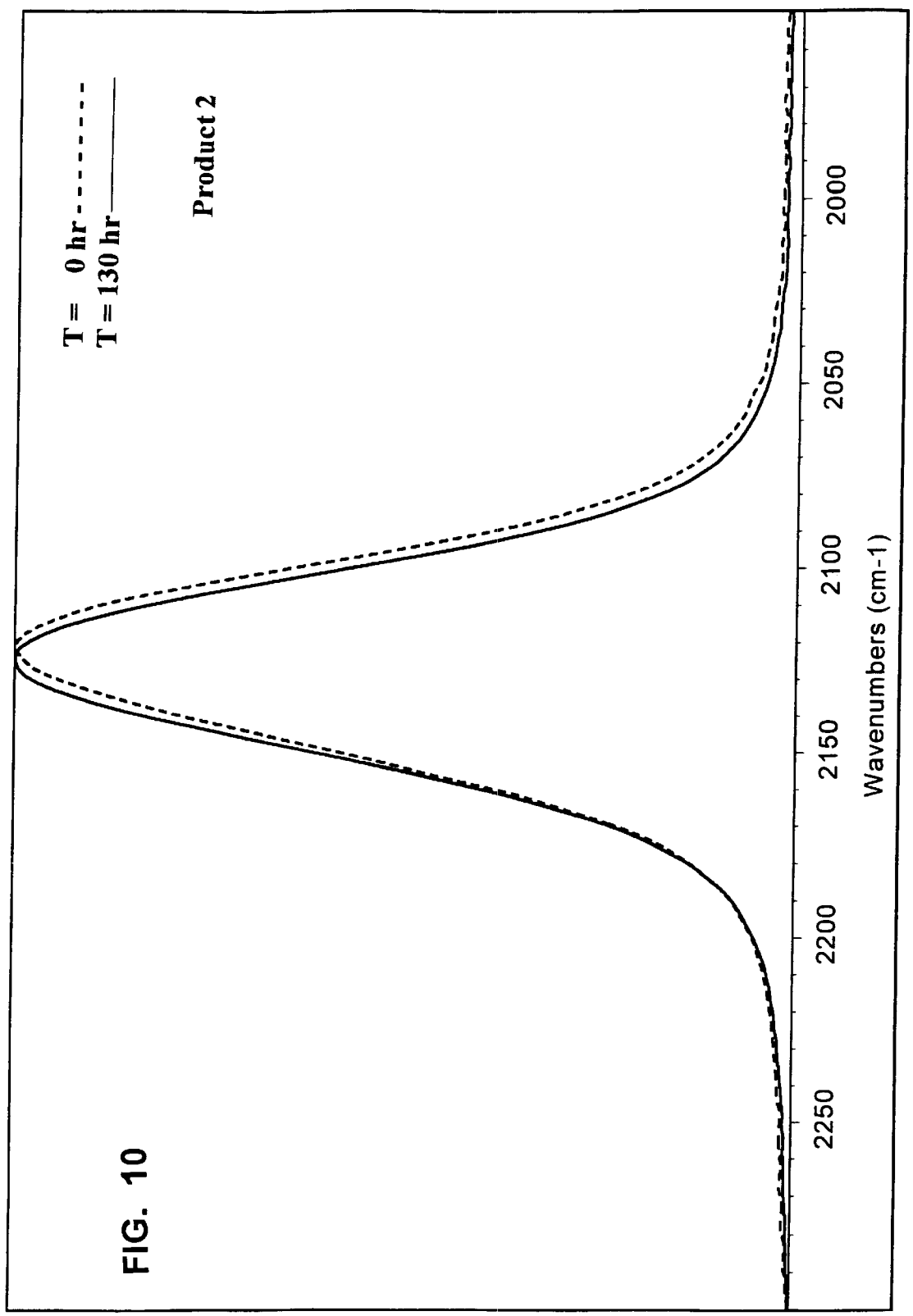
FIGS. 10 and 11 graphically represent the FTIR spectra of Product 2 at t=0 and t=130 hours into the polymerization process.
Figure 11:
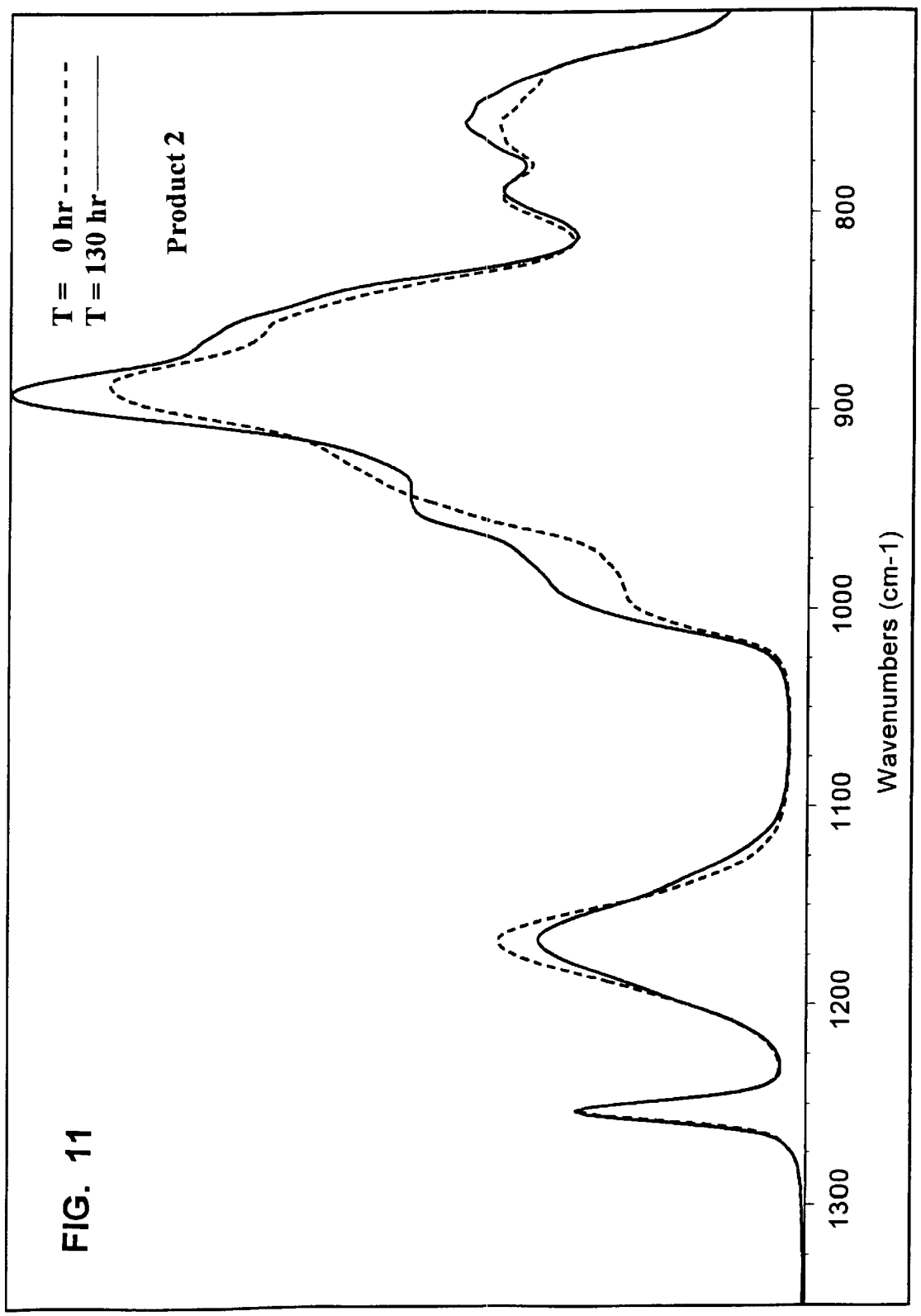

In FIGS. 10 and 11 illustrating the changes in Product 2 it is evident that there were only minor, if any, changes in the ammonolysis product between the initial sampling at approximately zero hrs and 130 hrs later. In FIG. 10 it is shown that the Si—H bond environment is virtually unchanged as indicated by the peak at approximately 2120 cm$^{-1}$. At approximately 1170 cm$^{-1}$ there is a reduction in the Si—NH environment because remaining amine end groups on linear chains continue to form additional small cyclic polymers. These small cyclic polymers form because the linear chains are not stabilized in the acidic ammonia rich environment such as Product 1. It is also evident from the spectral changes between 800 and 1000 cm$^{-1}$ that the polymers were continuing to evolve from short linear chains to small cyclic rings. Clearly, as shown by the spectra, Product 2 made minor alterations during the course of the 130 hours reaction demonstrating that once the initial product was formed and intermixed with the precipitated ammonium halide salt no further reaction occurred except for continued minor rearrangement from linear to cyclic compounds as predisposed by the prior art methods.

In contrast, Product 1 shows a marked progression wherein the novel compounds of the present invention pass through several different structures to at least some higher molecular weight fused ring structures. As shown in FIG. 4, the initial precursor ammonolysis product has a lessor degree of amine (Si—NH) functionality at 1170 cm$^{-1}$ that increases over time to reach a maximum at approximately 106 hrs. As the reaction proceeds to 130 hrs it is shown that there is a reduction in amine character of the compounds which provides additional proof of condensation to a fused ring structure with an increased amount of Si—N character where nitrogen atoms are bonded to three silicon atoms. The evidence of this condensation to a fused cyclic structure can be gleaned from the calculated areas under the peaks, the peaks found in the region of the FTIR spectra ranging from approximately 1234 cm$^{-1}$ to about 1060 cm$^{-1}$. As shown below in Table 3, growth in the area under the curve is increasing until approximately 130 hours into the polymerization process at which time the area under the curve starts to decrease. This is indicative of a reduction in the Si—NH character of the polymer with a concomitant increase in Si—N functionality. Growth in a shoulder at approximately 1000 cm$^{-1}$ to 900 cm$^{-1}$ is believed to represent Si—N bonds in which the nitrogen atom is not bonded to hydrogen. All of this data supports a more condensed Product 1 structure which results from Si—H bond cleavage, further ammonolysis in the liquid ammonia, and subsequent further polymer condensation.

TABLE 3

| Sample | 1 | 2 | 3 | 4 | 5 | 6 | 7 |
|---|---|---|---|---|---|---|---|
| Time (hrs) | 2.5 | 6,5 | 12 | 72 | 84 | 106 | 130 |
| Area under the curve | 9.255 | 9.507 | 9.719 | 10.267 | 10.724 | 11.231 | 10.899 |

Results: The spectra of Product 1 shows the progression of the reaction with a decrease of Si—H bonds and an increase in Si—N—H bonds indicating novel silazanes and/or polysilazanes having increased Si—N linkages with a concomitant reduction in Si—H bonds. In contrast, Product 2 remained unchanged after initial formation. The difference in the spectra of the Product 1 and 2 shows that Product 1 prepared by the method of the present invention is a new novel compound heretofore unknown.

EXAMPLE 7

Preparation of Methylvinylmethylhydridopolysilazane Using the Method of the Present Invention A polysilazane was prepared using the methods of the present invention as described in Example 1, by the ammonolysis of a mixture of 80% wt of methyldichlorosilane and 20% wt of vinylmethyldichlorosilane.

The reaction mixture was analyzed by Nuclear Magnetic Resonance ($^1$H NMR) to determine conversion of the silanes to the novel silazane and polysilazanes of the present invention. Also, $^1$H NMR analysis of the ammonolysis products at different times (t=6.5 hrs., 72 hrs. and 84 hrs.) during the reaction was helpful in characterizing the product, since quantitative measurements of the amount of Si—H (4.2–4.8 ppm) and Si—NH (0.5 to 1.0 ppm) bonds could be determined based on the constancy of the intensity of the Si—CH$_3$ (0 to 0.3 ppm) signal. The series of ammonolysis products exhibited a decreased intensity of Si—H signals with increasing time in the ammonolysis process. For ammonolysis products analyzed at t=6.5 hours, a CH$_3$ to NH proton ratio of about 2.8:1 was determined. This ratio is close to the theoretical ratio of 3/0:1 for CH$_3$ to NH protons in a linear polysilazane copolymer having the formula [(Vi)(Me)Si—NH—]0.2[—(H)(Me)Si—NH—]0.8.

For the ammonolysis products at t=72 hours, a CH$_3$ to NH proton ratio of about 2.3:1 was determined. This ratio indicates a higher degree of Si—NH bonding in the polymer than in the linear structure, and approaches the theoretical ratio of 2.1:1 for a condensed polysilazane copolymer having the ideal formula [—(Vi)(Me)Si—NH—]0.2[—(H)(Me)Si(NH)½—NH—]0.8. Such a structure can be achieved by total Si—H bond cleavage, with the formation of new Si—NH bonds, and can be envisioned as having chain segments in which sequential [—(H)(Me)Si—NH—] units have condensed with similar repeats unit in another polymer chain to generate a "ladderlike" structure as shown in Structure 2.

For the ammonolysis product at t=84 hours, the CH$_3$ to NH proton ratio was 2.7:1, indicating a lower degree of Si—NH bonding in the polymer than in the "ladderlike" condensed structure. This would indicate a further condensation of the structure with the cleavage of N—H bonds to give nitrogen atoms which are bonded to three silicon atoms as shown in Structure 1. The ideal formula for such a polymer would be [—Vi)(Me)Si—NH—]0.2[—(Me)Si(N)—]0.8 if just the "ladderlike" structures of the intermediate condensation product described above underwent further condensation. The theoretical ratio of CH$_3$ protons to NH protons in this polymer would be 15:1, indication that just a minor fraction of the polymer undergoes this second condensation step. Since a small number of residual Si—H bonds are always detected by both FTIR and $^1$H NMR techniques, even in polymers which have been subjected to very long periods of ammonolysis, it is likely that such polymers comprise a variety of bond schemes, including, but not limited to linear structures, "ladderlike" structures, fused cyclic structures, and ring structures of a variety of sizes, all in the same ammonolysis product.

Results: The evolution of polymer structures shown in the example provides evidence that the initially formed ammonolysis product prepared by the method of the present invention progresses through a series of condensations, first involving the cleavage of Si—H bonds in the newly formed ammonolysis product to form high molecular weight linear polysilazanes, then the addition of ammonia to the product to generate new Si—NH bonds, and then further condensation to result in products containing a reduced number of N—H bonds compared to the intermediate compositions. Such final compositions may comprise a variety of polysilazane structures, including linear and cyclic in a variety of sizes having a wide spectrum of connectivities.

EXAMPLE 8

Ammonolysis of Dichloromethylsilane Using the Method of the Present Invention showing Increased Viscosity of Product Using the same general procedure of the present invention as outlined in Example 1, a polysilazane was prepared using 1601.4 grams of methyldichlorosilane. Samples of the ammonolysis products were withdrawn during the process to analyzed the viscosity of the polymers.

Results: As shown in Table 4 below, as the polymerization process progressed there was an concomitant increase in the viscosity of the polysilazane. Samples 7 and 8 were soft and firm gels, respectively, and as such, viscosity analysis was discontinued.

TABLE 4

| Sample | 1 | 2 | 3 | 4 | 5 | 6 | 7 | 8 |
|---|---|---|---|---|---|---|---|---|
| Time (hrs) | 0 | 0.5 | 1.5 | 2.5 | 3.5 | 4.5 | 5.5 | 6.5 |
| Viscosity (cp) | 26.11 | 43.52 | 216.44 | 1003.52 | 8304.64 | 17100.80 | — | — |

That which is claimed is:

1. A silazane or polysilazane comprising a reduced amount of Si—H bonds relative to the quantity of Si—H bonds that are incorporated into the silazane or polysilazane from a starting compound comprising at least one Si—H bond and at least one Si-halide bond, said silazane or polysilazane further comprising a greater number of Si—N bonds and a greater nitrogen content than would otherwise be derived from complete ammonolysis of the Si-halide bonds of said starting compound.

2. The silazane or polysilazane according to claim 1 having at least 10% fewer Si—H bonds than in the Si—H bond containing starting compound.

3. The silazane or polysilazane according to claim 1 having at least 90% fewer Si—H bonds than in the Si—H bond containing starting compound.

4. The silazane or polysilazane according to claim 1 wherein a reduction in Si—H bonds is proportional to an increase in viscosity of the silazane or polysilazane.

5. The silazane or polysilazane according to claim 1 wherein the reduction in Si—H bonds ranges from about 10% to about 90% relative to the number of Si—H bonds contained in the starting compound.

6. The silazane or polysilazane according to claim 5 further comprising nitrogen atoms which are not bonded to hydrogen.

7. The silazane or polysilazane according to claim 1 wherein the Si—H bond containing starting compound is a halosilane.

8. The silazane or polysilazane according to claim 7 wherein the halosilane starting compound is a member selected from the group consisting of $RSiX_3$, $R_2SiX_2$, $R_3SiX$, and mixtures thereof wherein R may be identical or different from each other, selected from the following group consisting of a hydrogen atom, a substituted or unsubstituted alkyl group, a substituted or unsubstituted cycloalkyl group, a substituted or unsubstituted alkenyl group or a substituted or unsubstituted aryl group, with the proviso that at least one R is a hydrogen atom, and X is a halogen.

9. The silazane or polysilazane according to claim 8 further comprising a halosilane selected from the group consisting of $RSiX_3$, $R_2SiX_2$, $R_3SiX$, and mixtures thereof wherein R may be identical or different from each other, selected from the following group including a substituted or unsubstituted alkyl group, a substituted or unsubstituted cycloalkyl group, a substituted or unsubstituted alkenyl group or a substituted or unsubstituted aryl group, and X is a halogen.

10. The silazane or polysilazane according to claim 1 wherein the compound has a structural segment selected from the group consisting of cyclic silazanes, linear silazanes and mixtures thereof.

11. A silazane or polysilazane product prepared by an ammonolysis reaction in anhydrous liquid ammonia with a starting compound comprising at least one Si—H bond and at least one Si-halide bond, said silazane or polysilazane product characterized by repeating units of silicon-nitrogen in a polymeric compound having a reduced amount of Si—H bonds relative to those in the starting compound, and further comprising a greater number of Si—N bonds and a greater nitrogen content than would otherwise be derived from complete ammonolysis of the Si-halide bonds of said starting compound.

12. A method for preparing a novel silazane and/or polysilazane by ammonolysis, the method comprising:
   a) introducing at least one halosilane having at least one Si—H bond into liquid anhydrous ammonia, the amount of liquid anhydrous ammonia being at least twice the stoichiometric amount of silicon-halide bonds on the halosilane, the halosilane reacting with the anhydrous liquid ammonia to form a precursor ammonolysis product and an ammonium halide salt or acid thereof, the ammonium halide salt or acid thereof being solubilized and ionized in the anhydrous liquid ammonia thereby providing an acidic environment; and
   b) maintaining the precursor ammonolysis product in the acidic environment for a sufficient time to reduce the number of Si—H bonds relative to the quantity of Si—H bonds that are incorporated into the novel silazane and/or polysilazane from the halosilane of step (a).

13. The method according to claim 12 wherein the anhydrous liquid ammonia is maintained at a sufficient temperature and pressure to remain in a liquefied state.

14. The method according to claim 13 wherein the temperature is maintained by venting anhydrous liquid ammonia as a gas.

15. The method according to claim 12 wherein the ammonium halide salt or acid derived therefrom forms an acidic environment in the anhydrous liquid ammonia to catalyze cleavage of a Si—H bond on the novel silazane and/or polysilazane.

16. The method according to claim 12 having no inert solvent introduced therein.

17. The method according to claim 12 further comprising separating the novel silazanes and/or polysilazanes to a liquid-layer distinct from the anhydrous liquid ammonia layer containing the solubilized ammonium halide.

18. The method according to claim 12 wherein the halosilane may be selected from the group consisting of $RSiX_3$, $R_2SiX_2$, $R_3SiX$, and mixtures thereof wherein R may be identical or different from each other, selected from the group including a hydrogen atom, a substituted or unsubstituted alkyl group, a substituted or unsubstituted cycloalkyl group, a substituted or unsubstituted alkenyl group or a substituted or unsubstituted aryl group, with the proviso that at least one R is a hydrogen atom, and X is a halogen.

19. The method according to claim 12 wherein the halosilane is introduced into the anhydrous liquid ammonia in the absence of an inert solvent.

20. A novel silazane and/or polysilazane prepared according to the method of claim 12.

21. A novel silazane and/or polysilazane prepared according to the method of claim 18.

22. The method according to claim 18 further comprising a halosilane selected from the group consisting of $RSiX_3$, $R_2SiX_2$, $R_3SiX$, and mixtures thereof wherein R may be identical or different from each other, selected from the following group including a alkyl group, a substituted or unsubstituted cycloalkyl group, a substituted or unsubstituted alkenyl group or a substituted or unsubstituted aryl group, and X is a halogen.

23. A method for preparing an ammonolysis product, the method comprising introducing at least one halogen substituted silane into anhydrous liquid ammonia at a temperature in a range at or below −33° C. to about 130° C., the amount of anhydrous liquid ammonia being at least twice the stoichiometric amount of silicon-halide bonds on the halogen substituted silane, the halogen substituted silane reacting with the anhydrous liquid ammonia to form an ammonolysis product and an ionic by-product solubilized in the anhydrous liquid ammonia.

24. The method according to claim 23 wherein the anhydrous liquid ammonia is maintained at a sufficient temperature and pressure to remain in a liquefied state during the entire process.

25. The method according to claim 23 wherein the reaction mixture has no inert solvent introduced therein.

26. The method according to claim 23 further comprising separating the ammonolysis product as a liquid-layer distinct from the anhydrous liquid ammonia layer containing the solubilized ionic by-product.

27. The method according to claim 23 wherein the halogen substituted silane is a halosilane selected from the group consisting of $RSiX_3$, $R_2SiX_2$, $R_3SiX$, and mixtures thereof wherein R may be identical or different from each other, selected from the following group including a hydrogen atom, a alkyl group, a substituted or unsubstituted cycloalkyl group, a substituted or unsubstituted alkenyl group or a substituted or unsubstituted aryl group, and X is a halogen.

28. A method for preparing an ammonolysis product, which comprises the steps of introducing an ionizable salt into anhydrous liquid ammonia, introducing at least one halogen substituted silane into said anhydrous liquid ammonia with said ionizable salt, the amount of said anhydrous liquid ammonia being at least twice the stoichiometric amount of silicon-halide bonds on the halogen substituted silane, the halogen substituted silane reacting with the anhydrous liquid ammonia to form an ammonolysis product and an ionic by-product solubilized in the anhydrous liquid ammonia.

29. The method according to claim 28 wherein the ionizable salt is a member selected from the group consisting of ammonium halide, ammonium nitrate, and ammonium acetate.

30. The method according to claim 23 wherein the halogen substituted silanes are introduced into the anhydrous liquid ammonia in the absence of an inert solvent.

31. The ammonolysis product prepared according to the method of claim 23.

32. The ammonolysis product prepared according to the method of claim 28.

33. The ammonolysis product prepared according to the method of claim 29.

34. A method for removing an ammonium halide salt from an ammonolysis product to provide a purified ammonolysis product, the method comprising:
   a) mixing the ammonolysis product containing the ammonium halide salt with a sufficient amount of anhydrous liquid ammonia at a temperature in a range at or below −33° C. to about 130° C. to solubilize the ammonium halide salt;
   b) discontinuing the mixing step to allow the mixture to separate into distinct layers, wherein the ammonolysis product is retained in a separate liquid layer distinct from the anhydrous liquid ammonia comprising the solubilized ammonium halide salt, and
   c) separating the purified ammonolysis product from the anhydrous liquid ammonia.

35. The method according to claim 34 wherein the ammonolysis product is a member selected from the group consisting of a silazane, polysilazane, organosilazane, organopolysilazane and mixtures thereof.

36. A method for removing an ammonium halide salt from an ammonolysis product to provide a purified ammonolysis product, the method comprising:
   a) mixing the ammonolysis product containing the ammonium halide salt with a sufficient amount of anhydrous liquid ammonia to solubilize the ammonium halide salt; and
   b) introducing at least a stoichiometric amount of an alkali metal or alkaline earth metal into the anhydrous liquid ammonia to neutralize the ammonium halide salt and produce an alkali metal or alkaline earth metal halide salt.

37. The method according to claim 36 wherein the alkali metal or alkaline earth metal is selected from the group consisting of Li, Na, K, Ca and mixtures thereof.

38. A method for further polymerizing an ammonolysis product having an Si—H bond, the method comprising:
   a) providing a solution of anhydrous liquid ammonia having solubilized therein an acid catalyst;
   b) introducing an ammonolysis product having a Si—H bond into a stoichiometric excess of liquid anhydrous ammonia; and
   c) maintaining the ammonolysis product in contact with the anhydrous liquid ammonia having solubilized therein an acid catalyst for a sufficient time to polymerize, and/or copolymerize and/or rearrange ammonolysis products.

39. The method according to claim 38 wherein the acid catalyst is a nonmetallic acid catalyst selected from the group consisting of an ammonium halide, ammonium nitrate, ammonium acetate, and mixtures thereof.

40. The method according to claim 38 wherein the acid catalyst ionizes in the anhydrous liquid ammonia and produces an acidic environment.

41. The method according to claim 38 wherein the ammonolysis product is a member selected from the group consisting of a silazane, polysilazane, aminosilane, organosilazane, organopolysilazane and mixtures thereof.

42. The method according to claim 41 wherein the acid catalyst is effective in facilitating the cleavage of the Si—H bond.

43. A method for increasing the viscosity of a liquid ammonolysis product, the method comprising:
   a) introducing the liquid ammonolysis product into a sufficient amount of anhydrous liquid ammonia to dissolve the ammonolysis product therein;
   b) introducing a catalytically effective amount of an alkali or alkaline earth metal into the anhydrous liquid ammonia containing the ammonolysis product, the alkali or alkaline earth metal producing solvated electrons and cations therein; and
   c) maintaining the ammonolysis product in the anhydrous liquid ammonia for a sufficient time to increase the viscosity of the ammonolysis product.

44. The method according to claim 43 further comprising quenching the reaction with the addition of an acidic reagent.

45. The method according to claim 43 further comprising separating the modified ammonolysis product from the anhydrous liquid ammonia.

46. The method according to claim 43 wherein the viscosity is controllably increased to a solid material.

47. The method according to claim 43 wherein the ammonolysis product is a member selected from the group consisting of a silazane, polysilazane, organosilazane, organopolysilazane and mixtures thereof.

48. The method according to claim 43 wherein the alkali or alkaline earth metal is a member selected from the group consisting of Li, Na, K, Ca and mixtures thereof.

49. A product prepared according to the method of claim 43.

50. The product according to claim 43 wherein the viscosity of the product is controllable by contact time and the type and amount of the alkali or alkaline earth metal catalyst.

51. The method according to claim 43 wherein the ammonolysis product contains at least one Si—H bond.

52. The method according to claim 43 wherein the liquid ammonolysis product is prepared according to claim 11.

53. The method according to claim 42 wherein the liquid ammonolysis product is prepared according to claim 19.

54. A silazane or polysilazane product comprising a reduced amount of Si—H bonds relative to the quantity of Si—H bonds that are incorporated into the silazane or polysilazane product from a starting compound comprising a silazane or polysilazane with at least one Si—H bond, said silazane or polysilazane product further comprising a greater number of Si—N bonds and a greater nitrogen content than said starting compound.

55. The silazane or polysilazane product according to claim 54 comprising at least 10% fewer Si—H bonds than in the Si—H bond containing starting compound.

56. The silazane or polysilazane product according to claim 54 comprising at least 90% fewer Si—H bonds than in the Si—H bond containing starting compound.

57. The silazane or polysilazane product according to claim 54 wherein the reduction in Si—H bonds is proportional to an increase in viscosity of the silazane or polysilazane product.

58. The silazane or polysilazane product according to claim 54 wherein the reduction in Si—H bonds ranges from about 10% to about 90% relative to the Si—H bonds contained in the starting compound.

59. The silazane or polysilazane product according to claim 58 further comprising nitrogen atoms which are not bonded to hydrogen.

60. The silazane or polysilazane product according to claim 54 wherein the Si—H bond containing starting compound is a silazane.

61. The silazane or polysilazane product according to claim 54 wherein the Si—H bond containing starting compound is a polysilazane.

62. The silazane or polysilazane product according to claim 54 wherein the product comprises a structural segment selected from the group consisting of cyclic silazanes, linear silazanes and mixtures thereof.

63. A silazane or polysilazane product prepared by an ammonolysis reaction in anhydrous liquid ammonia with a silazane or polysilazane starting compound comprising at least one Si—H bond, said silazane or polysilazane product characterized by repeating units of silicon-nitrogen in a polymeric compound having a reduced amount of Si—H bonds relative to those in the starting compound, and further comprising a greater number of Si—N bonds and a greater nitrogen content than said starting compound.

* * * * *